US005439814A

United States Patent [19]

Frey et al.

[11] Patent Number: 5,439,814

[45] Date of Patent: Aug. 8, 1995

[54] DNA ENCODING INFECTIOUS RUBELLA VIRUS

[75] Inventors: Teryl K. Frey, Atlanta; Geraldina Dominguez, Tucker; Chin-Yen Wang, Clarkston, all of Ga.

[73] Assignee: Georgia State Research Foundation, Inc., Atlanta, Ga.

[21] Appl. No.: 93,453

[22] Filed: Jul. 19, 1993

Related U.S. Application Data

[63] Continuation of Ser. No. 722,334, Jun. 28, 1991, abandoned.

[51] Int. Cl.[6] ........................ C12N 15/00; C12N 7/00; C12N 15/40; C12N 15/63

[52] U.S. Cl. .............................. 435/172.3; 536/23.72; 435/235.1; 435/320.1

[58] Field of Search .......................... 536/23.71, 23.72; 435/235.1, 320.1, 172.3; 424/89, 93 A, 219.1, 185.1; 935/65, 57, 32

[56] References Cited

PUBLICATIONS

Callahan, P. L. et al. 1985. *Proc. Natl. Acad. Sci.* USA vol. 82 pp. 732–736.
Cunningham, A. L. et al. 1985. *J. Infect. Dis.* vol. 15 pp. 638–645.
Mizutani, S. et al. 1985. *J. Virol.* vol. 56 pp. 628–632.
Ahlquist, P. et al. 1984. *Proc. Natl. Acad. Sci.* USA vol. 91 pp. 7066–7070.
Ahlquist, P. et al 1984. *J. Mol. Biol.* vol. 172 pp. 369–383.
Ahlquist, P. et al. 1984. *Mol. Cell. Biol.* vol. 4 pp. 2876–2882.
Ou, J. H. et al. 1983. *J. Mol. Biol.* vol. 168 pp. 1–15.
Frey, T. K. et al. 1989. *Virol.* vol. 168 pp. 191–194.
Niesters, H. G. M. et al. 1990. *J. Virol.* vol. 64 pp. 4162–4168.
Weibel, R. E. et al. 1980, *Proc. Soc. Exp. Biol. Med.* vol 165, pp. 44–49.
Waxham and Wolinsky, *Virology* 126:194–203 (1983).
Oker-Blom, et al., *J. Virol.* 46:964–973 (1983).
Waxham and Wolinsky, *Virology* 143:153–165 (1985).
Green and Dorsett, *J. Virol.* 57:893–898 (1986).
Oker-Blom, *J. Virol.* 51:354–358 (1984).
Rice, et al., *Virology* 61:3809–3819 (1987).
Frey, et al., *Virology* 154:228–232 (1986).
Nakhasi, et al. *J. Biol. Chem.* 261:16616–16621 (1986).
Clarke, et al. *Nucleic Acids Res.* 15:3041–3057 (1987).
Vidgren, et al., *J. gen. Virol.* 68:2347–2357 (1987).
Takkinen, et al. *J. gen. Virol.* 69:603–612 (1988).
Frey and Marr, *Gene* 62:85–99 (1988).
Dominguez, et al. *Virology* 177:225–238 (Jul., 1990).
Ballart, I. et al. 1991, *EMBO J.* vol. 10 (11) p. 3558.
Hovi, T. et al. 1970. *Virology* vol. 42 pp. 1–8.
Zheng, D. et al. 1989. *Gene* vol. 82 pp. 343–349.
Davis, N. L. et al. 1989. *Virology* vol. 171 pp. 189–204.

*Primary Examiner*—Mary E. Mosher
*Attorney, Agent, or Firm*—Jones & Askew

[57] ABSTRACT

The entire rubella virus genomic RNA has been sequenced. An infectious cDNA clone has been constructed. Mutants of this clone that are rendered nonpathogenic are used as vaccines to vaccinate humans, including pregnant or older women, with decreased risk of causing fetal infection, autoimmune disease or neurological symptoms.

5 Claims, 6 Drawing Sheets

Page 1 of 3

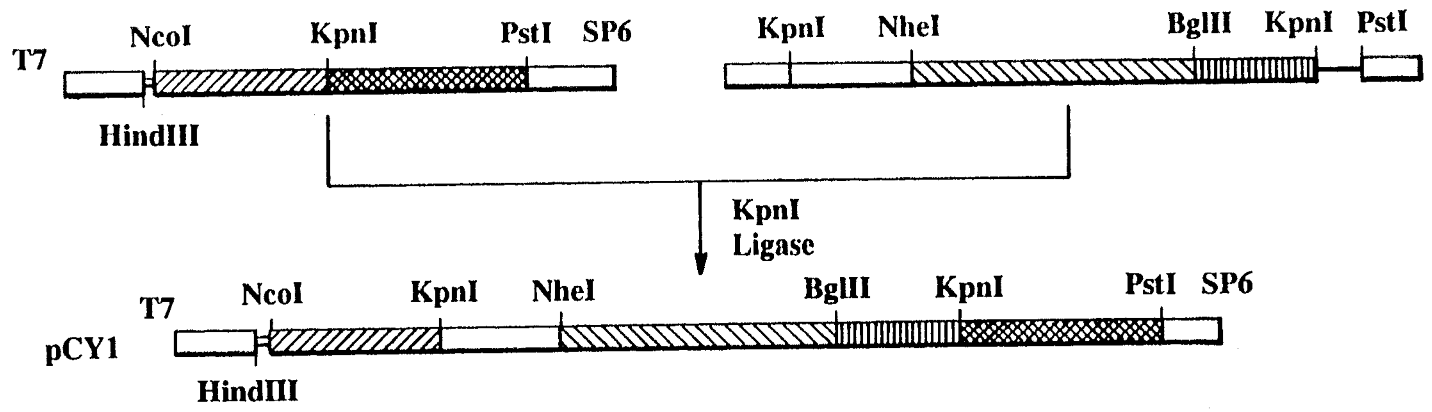

Mutagenic oligo

SpeI HindIII

5' AGCTACTAGTCTAAGCTTTCGGACCTCGCTTAGGACTCCCATTCC 3'
TGATCAGATTCGAAAGCCTGGAGCGAATCCTGAGGGTAAGGGTAC

FIG. 2A

Page 2 of 3

5' end modification :

Primer 1 TTCGAAGCTTATTTAGGTCACACTATA
GCATGGAAGCTATCGGACCTC

Primer 2 TGGTCTCTTACCCAACT
AAAA RUB RNA
Primer 2

3' end modification :

Primer 3 GATGCATCCCTATAGTGAGTCGTATTAG

Primer 4 AATTCTAATACAACTCACTATAGGGATG
CATCTGCA

Primer 5 AATGCCCGAGTGGATCCA

Primer 6 ACGTGCATGCCTGCAGTTTTTTTTTTTT
TTTTTTTT

Page 3 of 3

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 9757 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:1:

CAAUGGAAGC UAUCGGACCU CGCUUAGGAC UCCCAUUCCC AUGGAGAAAC UCCUAGAUGA 60

GGUUCUUGCC CCCGGUGGGC CUUAUAACUU AACCGUCGGC AGUUGGGUAA GAGACCACGU 120

CCGAUCAAUU GUCGAGGGCG CGUGGGAAGU GCGCGAUGUU GUUACCGCUG CCCAAAAGCG 180

GGCCAUCGUA GCCGUGAUAC CCAGACCUGU GUUCACGCAG AUGCAGGUCA GUGAUCACCC 240

AGCACUCCAC GCAAUUUCGC GGUAUACCCG CCGCCAUUGG AUCGAGUGGG GCCCUAAAGA 300

AGCCCUACAC GUCCUCAUCG ACCCAAGCCC GGGCCUGCUC CGCGAGGUCG CUCGCGUUGA 360

GCGCCGCUGG GUCGCACUGU GCCUCCACAG GACGGCACGC AAACUCGCCA CCGCCCUGGC 420

CGAGACGGCC AGCGAGGCGU GGCACGCUGA CUACGUGUGC GCGCUGCGUG GCGCACCGAG 480

CGGCCCCUUC UACGUCCACC CUGAGGACGU CCCGCACGGC GGUCGCGCCG UGGCGGACAG 540

AUGCUUGCUC UACUACACAC CCAUGCAGAU GUGCGAGCUG AUGCGUACCA UUGACGCCAC 600

CCUGCUCGUG GCGGUUGACU UGUGGCCGGU CGCCCUUGCG GCCCACGUCG GCGACGACUG 660

GGACGACCUG GGCAUUGCCU GGCAUCUCGA CCAUGACGGC GGUUGCCCCG CCGAUUGCCG 720

CGGAGCCGGC GCUGGGCCCA CGCCCGGCUA CACCCGCCCC UGCACCACAC GCAUCUACCA 780

AGUCCUGCCG GACACCGCCC ACCCCGGGCG CCUCUACCGG UGCGGGCCCC GCCUGUGGAC 840

GCGCGAUUGC GCCGUGGCCG AACUCUCAUG GGAGGUUGCC CAACACUGCG GGCACCAGGC 900

GCGCGUGCGC GCCGUGCGAU GCACCCUCCC UAUCCGCCAC GUGCGCAGCC UCCAACCCAG 960

CGCGCGGGUC CGACUCCCGG ACCUCGUCCA UCUCGCCGAG GUGGGCCGGU GGCGGUGGUU 1020

CAGCCUCCCC CGCCCCGUGU UCCAGCGCAU GCUGUCCUAC UGCAAGACCC UGAGCCCCGA 1080

-continued

CGCGUACUAC AGCGAGCGCG UGUUCAAGUU CAAGAACGCC CUGUGCCACA GCAUCACGCU 1140

CGCGGGCAAU GUGCUGCAAG AGGGGUGGAA GGGCACGUGC GCCGAGGAAG ACGCGCUGUG 1200

CGCAUACGUA GCCUUCCGCG CGUGGCAGUC UAACGCCAGG UUGGCGGGGA UUAUGAAAGG 1260

CGCGAAGUGC GCCGCCGACU CUUUGAGCGU GGCCGGCUGG CUGGACACCA UUUGGGACGC 1320

CAUUAAGCGG UUCCUCGGUA GCGUGCCCCU CGCCGAGCGC AUGGAGGAGU GGGAACAGGA 1380

CGCCGCGGUC GCCGCCUUCG ACCGCGGCCC CCUCGAGGAC GGCGGGCGCC ACUUGGACAC 1440

CGUGCAACCC CCAAAAUCGC CGCCCCGCCC UGAGAUCGCC GCGACCUGGA UCGUCCACGC 1500

AGCCAGCGAA GACCGCCAUU GCGCGUGCGC UCCCCGCUGC GACGUCCCGC GCGAACGUCC 1560

UUCCGCGCCC GCCGGCCAGC CGGAUGACGA GGCGCUCAUC CCGCCGUGGC UGUUCGCCGA 1620

GCGCCGUGCC CUCCGCUGCC GCGAGUGGGA UUUCGAGGCU CUCCGCGCGC GCGCCGAUAC 1680

GGCGGCCGCG CCCGCCCCGC CGGCUCCACG CCCCGCGCGG UACCCCACCG UGCUCUACCG 1740

CCACCCCGCC CACCACGGCC CGUGGCUCAC CCUUGACGAG CCGGGCGAGG CUGACGCGGC 1800

CCUGGUCUUA UGCGACCCAC UUGGCCAGCC GCUCCGGGGC CCUGAACGCC ACUUCGCCGC 1860

CGGCGCGCAU AUGUGCGCGC AGGCGCGGGG GCUCCAGGCU UUUGUCCGUG UCGUGCCUCC 1920

ACCCGAGCGC CCCUGGGCCG ACGGGGGCGC CAGAGCGUGG GCGAAGUUCU UCCGCGGCUG 1980

CGCCUGGGCG CAGCGCUUGC UCGGCGAGCC AGCAGUUAUG CACCUCCCAU ACACCGAUGG 2040

CGACGUGCCA CAGCUGAUCG CACUGGCUUU GCGCACGCUG GCCCAACAGG GGGCCGCCUU 2100

GGCACUCUCG GUGCGUGACC UGCCCGGGGG UGCAGCGUUC GACGCAAACG CGGUCACCGC 2160

CGCCGUGCGC GCUGGCCCCC GCCAGUCCGC GGCCGCGUCA CCGCCACCCG GCGACCCCCC 2220

GCCGCCGCGC CGCGCACGGC GAUCGCAACG GCACUCGGAC CGUCGCGGCA CUCCGCCCCC 2280

CGCGCCUGCG CGCGACCCGC CGCCGCCCGC CCCCAGCCCG CCCGCGCCAC CCCGCGCUGG 2340

UGACCCGGUC CCUCCCAUUC CCGCGGGGCC GGCGGAUCGC GCGCGUGACG CCGAGCUGGA 2400

GGUCGCCUGC GAGCCGAGCG GCCCCCCCAC GUCAACCAGG GCAGACCCAG ACAGCGACAU 2460

CGUUGAAAGU UACGCCCGCG CCGCCGGACC CGUGCACCUC CGAGUCCGCG ACAUCAUGGA 2520

CCCACCGCCC GGCUGCAAGG UCGUGGUCAA CGCCGCCAAC GAGGGGCUAC UGGCCGGCUC 2580

UGGCGUGUGC GGUGCCAUCU UUGCCAACGC CACGGCGGCC CUCGCUGCAA ACUGCCGGCG 2640

CCUCGCCCCA UGCCCCACCG GCGAGGCAGU GGCGACACCC GGCCACGGCU GCGGGUACAC 2700

CCACAUCAUC CACGCCGUCG CGCCGCGGCG UCCUCGGGAC CCCGCCGCCC UCGAGGAGGG 2760

CGAAGCGCUG CUCGAGCGCG CCUACCGCAG CAUCGUCGCG CUAGCCGCCG CGCGUCGGUG 2820

GGCGUGUGUC GCGUGCCCCC UCCUCGGCGC UGGCGUCUAC GGCUGGUCUG CUGCGGAGUC 2880

CCUCCGAGCC GCGCUCGCGG CUACGCGCAC CGAGCCCGUC GAGCGCGUGA GCCUGCACAU 2940

CUGCCACCCC GACCGCGCCA CGCUGACGCA CGCCUCCGUG CUCGUCGGCG CGGGGCUCGC 3000

UGCCAGGCGC GUCAGUCCUC CUCCGACCGA GCCCCUCGCA UCUUGCCCCG CCGGUGACCC 3060

GGGCCGACCG GCUCAGCGCA GCGCGUCGCC CCCAGCGACC CCCCUUGGGG AUGCCACCGC 3120

GCCCGAGCCC CGCGGAUGCC AGGGGUGCGA ACUCUGCCGG UACACGCGCG UCACCAAUGA 3180

CCGCGCCUAU GUCAACCUGU GGCUCGAGCG CGACCGCGGC GCCACCAGCU GGGCCAUGCG 3240

CAUUCCCGAG GUGGUUGUCU ACGGGCCGGA GCACCUCGCC ACGCAUUUUC CAUUAAACCA 3300

CUACAGUGUG CUCAAGCCCG CGGAGGUCAG GCCCCCGCGA GGCAUGUGCG GGAGUGACAU 3360

GUGGCGCUGC CGCGGCUGGC AUGGCAUGCC GCAGGUGCGG UGCACCCCCU CCAACGCUCA 3420

CGCCGCCCUG UGCCGCACAG GCGUGCCCCC UCGGGCGAGC ACGCGAGGCG GCGAGCUAGA 3480

CCCAAACACC UGCUGGCUCC GCGCCGCCGC CAACGUUGCG CAGGCUGCGC GCGCCUGCGG 3540

-continued

CGCCUACACG AGUGCCGGGU GCCCCAAGUG CGCCUACGGC CGCGCCCUGA GCGAAGCCCG 3600

CACUCAUGAG GACUUCGCCG CGCUGAGCCA GCGGUGGAGC GCGAGCCACG CCGAUGCCUC 3660

CCCUGACGGC ACCGGAGAUC CCCUCGACCC CCUGAUGGAG ACCGUGGGAU GCGCCUGUUC 3720

GCGCGUGUGG GUCGGCUCCG AGCAUGAGGC CCCGCCCGAC CACCUCCUGG UGUCCCUUCA 3780

CCGUGCCCCA AAUGGUCCGU GGGGCGUAGU GCUCGAGGUG CGUGCGCGCC CCGAGGGGGG 3840

CAACCCCACC GGCCACUUCG UCUGCGCGGU CGGCGGCGGC CCACGCCGCG UCUCGGACCG 3900

CCCCCACCUC UGGCUUGCGG UCCCCCUGUC UCGGGGCGGU GGCACCUGUG CCGCGACCGA 3960

CGAGGGGCUG GCCCAGGCGU ACUACGACGA CCUCGAGGUG CGCCGCCUCG GGGAUGACGC 4020

CAUGGCCCGG GCGGCCCUCG CAUCAGUCCA ACGCCCUCGC AAAGGCCCUU ACAAUAUCAG 4080

GGUAUGGAAC AUGGCCGCAG GCGCUGGCAA GACUACCCGC AUCCUCGCUG CCUUCACGCG 4140

CGAAGACCUU UACGUCUGCC CCACCAAUGC GCUCCUGCAC GAGAUCCAGG CCAAACUCCG 4200

CGCGCGCGAU AUCGACAUCA AGAACGCCGC CACCUACGAG CGCCGGCUGA CGAAACCGCU 4260

CGCCGCCUAC CGCCGCAUCU ACAUCGAUGA GGCGUUCACU CUCGGCGGCG AGUACUGCGC 4320

GUUCGUUGCC AGCCAAACCA CCGCGGAGGU GAUCUGCGUC GGUGAUCGGG ACCAGUGCGG 4380

CCCACACUAC GCCAAUAACU GCCGCACCCC CGUCCCUGAC CGCUGGCCUA CCGAGCGCUC 4440

GCGCCACACU UGGCGCUUCC CCGACUGCUG GGCGGCCCGC CUGCGCGCGG GGCUCGAUUA 4500

UGACAUCGAG GGCGAGCGCA CCGGCACCUU CGCCUGCAAC CUUUGGGACG GCCGCCAGGU 4560

CGACCUUCAC CUCGCCUUCU CGCGCGAAAC CGUGCGCCGC CUUCACGAGG CUGGCAUACG 4620

CGCAUACACC GUGCGCGAGG CCCAGGGUAU GAGCGUCGGC ACCGCCUGCA UCCAUGUAGG 4680

CAGAGACGGC ACGGACGUUG CCCUGGCGCU GACACGCGAC CUCGCCAUCG UCAGCCUGAC 4740

CCGGGCCUCC GACGCACUCU ACCUCCACGA GCUCGAGGAC GGCUCACUGC GCGCUGCGGG 4800

GCUCAGCGCG UUCCUCGACG CCGGGGCACU GGCGGAGCUC AAGGAGGUUC CCGCUGGCAU 4860

UGACCGCGUU GUCGCCGUCG AGCAGGCACC ACCACCGUUG CCGCCCGCCG ACGGCAUCCC 4920

CGAGGCCCAA GACGUGCCGC CCUUCUGCCC CCGCACUCUG GAGGAGCUCG UCUUCGGCCG 4980

UGCCGGCCAC CCCCAUUACG CGGACCUCAA CCGCGUGACU GAGGGCGAAC GAGAAGUGCG 5040

GUACAUGCGC AUCUCGCGUC ACCUGCUCAA CAAGAAUCAC ACCGAGAUGC CCGGAACGGA 5100

ACGCGUUCUC AGUGCCGUUU GCGCCGUGCG GCGCUACCGC GCGGGCGAGG AUGGGUCGAC 5160

CCUCCGCACU GCUGUGGCCC GCCAGCACCC GCGCCCUUUU CGCCAGAUCC CACCCCCGCG 5220

CGUCACUGCU GGGGUCGCCC AGGAGUGGCG CAUGACGUAC UUGCGGGAAC GGAUCGACCU 5280

CACUGAUGUC UACACGCAGA UGGGCGUGGC CGCGCGGGAG CUCACCGACC GCUACGCGCG 5340

CCGCUAUCCU GAGAUCUUCG CCGGCAUGUG UACCGCCCAG AGCCUGAGCG UCCCCGCCUU 5400

CCUCAAAGCC ACCUUGAAGU GCGUAGACGC CGCCCUCGGC CCCAGGGACA CCGAGGACUG 5460

CCACGCCGCU CAGGGGAAAG CCGGCCUUGA GAUCCGGGCG UGGGCCAAGG AGUGGGUUCA 5520

GGUUAUGUCC CCGCAUUUCC GCGCGAUCCA GAAGAUCAUC AUGCGCGCCU UGCGCCCGCA 5580

AUUCCUUGUG GCCGCUGGCC AUACGGAGCC CGAGGUCGAU GCGUGGUGGC AGGCCCAUUA 5640

CACCACCAAC GCCAUCGAGG UCGACUUCAC UGAGUUCGAC AUGAACCAGA CCCUCGCUAC 5700

UCGGGACGUC GAGCUCGAGA UUAGCGCCGC UCUCUUGGGC CUCCCUUGCG CCGAAGACUA 5760

CCGCGCGCUC CGCGCCGGCA GCUACUGCAC CCUGCGCGAA CUGGGCUCCA CUGAGACCGG 5820

CUGCGAGCGC ACAAGCGGCG AGCCCGCCAC GCUGCUGCAC AACACCACCG UGGCCAUGUG 5880

CAUGGCCAUG CGCAUGGUCC CCAAAGGCGU GCGCUGGGCC GGGAUUUUCC AGGGUGACGA 5940

UAUGGUCAUC UUCCUCCCCG AGGGCGCGCG CAGCGCGGCA CUCAAGUGGA CCCCCGCCGA 6000

-continued

GGUGGGCUUG UUUGGCUUCC ACAUCCCGGU GAAGCACGUG AGCACCCCUA CCCCCAGCUU 6060
CUGCGGGCAC GUCGGCACCG CGGCCGGCCU CUUCCAUGAU GUCAUGCACC AGGCGAUCAA 6120
GGUGCUUUGC CGCCGUUUCG ACCCAGACGU GCUUGAAGAA CAGCAGGUGG CCCUCCUCGA 6180
CCGCCUCCGG GGGGUCUACG CGGCUCUGCC UGACACCGUU GCCGCCAAUG CUGCGUACUA 6240
CGACUACAGC GCGGAGCGCG UCCUCGCUAU CGUGCGCGAA CUUACCGCGU ACGCGGGGGC 6300
GCGGCCUCGA CCACCCGGCC ACCAUCGGCG CGCUCGAGGA GAUUCAGACC CCCUACGCGC 6360
GCGCCAAUCU CCACGACGCC GACUAACGCC CCUGUACGUG GGGCCUUUAA UCUUACCUAC 6420
UCUAACCAGG UCAUCACCCA CCGUUGUUUC GCCGCAUCUG GUGGGUACCC AACUUUUGCC 6480
AUUCGGGAGA GCCCCAGGGU GCCCGAAUGG CUUCUACUAC CCCCAUCACC AUGGAGGACC 6540
UCCAGAAGGC CCUCGAGGCA CAAUCCCGCG CCCUGCGCGC GGAACUCGCC GCCGGCGCCU 6600
CGCAGUCGCG CCGGCCGCGG CCGCCGCGAC AGCGCGACUC CAGCACCUCC GGAGAUGACU 6660
CCGGCCGUGA CUCCGGAGGG CCCCGCCGCC GCCGCGGCAA CCGGGGCCGU GGCCAGCGCA 6720
GGGACUGGUC CAGGGCCCCG CCCCCCCCGG AGGAGCGGCA AGAAACUCGC UCCCAGACUC 6780
CGGCCCCGAA GCCAUCGCGG GCGCCGCCAC AACAGCCUCA ACCCCCGCGC AUGCAAACCG 6840
GGCGUGGGGG CUCUGCCCCG CGCCCCGAGC UGGGGCCACC GACCAACCCG UUCCAAGCAG 6900
CCGUGGCGCG UGGCCUGCGC CCGCCUCUCC ACGACCCUGA CACCGAGGCA CCCACCGAGG 6960
CCUGCGUGAC CUCGUGGCUU UGGAGCGAGG GCGAAGGCGC GGUCUUUUAC CGCGUCGACC 7020
UGCAUUUCAC CAACCUGGGC ACCCCCCCAC UCGACGAGGA CGGCCGCUGG GACCCUGCGC 7080
UCAUGUACAA CCCUUGCGGG CCCGAGCCGC CCGCUCACGU CGUCCGCGCG UACAAUCAAC 7140
CUGCCGGCGA CGUCAGGGGC GUUUGGGGUA AAGGCGAGCG CACCUACGCC GAGCAGGACU 7200
UCCGCGUCGG CGGCACGCGC UGGCACCGAC UGCUGCGCAU GCCAGUGCGC GGCCUCGACG 7260
GCGACAGCGC CCCGCUUCCC CCCCACACCA CCGAGCGCAU UGAGACCCGC UCGGCGCGCC 7320
AUCCUUGGCG CAUCCGCUUC GGUGCCCCCC AGGCCUUCCU UGCCGGGCUC UUGCUCGCCA 7380
CGGUCGCCGU UGGCACCGCG CGCGCCGGGC UCCAGCCCCG CGCUGAUAUG GCGGCACCUC 7440
CUACGCUGCC GCAGCCCCCC UGUGCGCACG GGCAGCAUUA CGGCCACCAC CACCAUCAGC 7500
UGCCGUUCCU CGGGCACGAC GGCCAUCAUG GCGGCACCUU GCGCGUCGGC CAGCAUUACC 7560
GAAACGCCAG CGACGUGCUG CCCGGCCACU GGCUCCAAGG CGGCUGGGGU UGCUACAACC 7620
UGAGCGACUG GCACCAGGGC ACUCAUGUCU GUCAUACCAA GCACAUGGAC UUCUGGUGUG 7680
UGGAGCACGA CCGACCGCCG CCCGCGACCC CGACGCCUCU CACCACCGCG GCGAACUCCA 7740
CGACCGCCGC CACCCCCGCC ACUGCGCCGG CCCCCUGCCA CGCCGGCCUC AAUGACAGCU 7800
GCGGCGGCUU CUUGUCUGGG UGCGGGCCGA UGCGCCUGCG CCACGGCGCU GACACCCGGU 7860
GCGGUCGGUU GAUCUGCGGG CUGUCCACCA CCGCCCAGUA CCCGCCUACC CGGUUUGGCU 7920
GCGCUAUGCG GUGGGGCCUU CCCCCCUGGG AACUGGUCGU CCUUACCGCC CGCCCCGAAG 7980
ACGGCUGGAC UUGCCGCGGC GUGCCCGCCC AUCCAGGCGC CCGCUGCCCC GAACUGGUGA 8040
GCCCCAUGGG ACGCGCGACU UGCUCCCCAG CCUCGGCCCU CUGGCUCGCC ACAGCGAACG 8100
CGCUGUCUCU UGAUCACGCC CUCGCGGCCU UCGUCCUGCU GGUCCCGUGG GUCCUGAUAU 8160
UUAUGGUGUG CCGCCGCGCC UGUCGCCGCC GCGGCGCCGC CGCCGCCCUC ACCGCGGUCG 8220
UCCUGCAGGG GUACAACCCC CCCGCCUAUG GCGAGGAGGC UUUCACCUAC CUCUGCACUG 8280
CACCGGGGUG CGCCACUCAA GCACCUGUCC CCGUGCGCCU CGCUGGCGUC CGUUUUGAGU 8340
CCAAGAUUGU GGACGGCGGC UGCUUUGCCC CAUGGGACCU CGAGGCCACU GGAGCCUGCA 8400
UUUGCGAGAU CCCCACUGAU GUCUCGUGCG AGGGCUUGGG GGCCUGGGUA CCCGCAGCCC 8460

-continued

| | | | | | | |
|---|---|---|---|---|---|---|
| UGCUCGCGCG | CAUCUGGAAU | GGCACACAGC | GCGCGUGCAC | CUUCUGGGCU | GUCAACGCCU | 8520 |
| ACUCCUCUGG | CGGGUACGCG | CAGCUGGCCU | CUUACUUCAA | CCCUGGCGGC | AGCUACUACA | 8580 |
| AGCAGUACCA | CCCUACCGCG | UGCGAGGUUG | AACCUGCCUU | CGGACACAGC | GACGCGGCCU | 8640 |
| GCUGGGGCUU | CCCCACCGAC | ACCGUGAUGA | GCGUGUUCGC | CCUUGCUAGC | UACGUCCAGC | 8700 |
| ACCCUCACAA | GACCGUCCGG | GUCAAGUUCC | AUACAGAGAC | CAGGACCGUC | UGGCAACUCU | 8760 |
| CCGUUGCCGG | CGUGUCGUGC | AACGUCACCA | CUGAACACCC | GUUCUGCAAC | ACGCCGCACG | 8820 |
| GACAACUCGA | GGUCCAGGUC | CCGCCCGACC | CCGGGGACCU | GGUUGAGUAC | AUUAUGAAUU | 8880 |
| ACACCGGCAA | UCAGCAGUCC | CGGUGGGGCC | UCGGGAGCCC | GAAUUGCCAC | GGCCCCGAUU | 8940 |
| GGGCCUCCCC | GGUUUGCCAA | CGCCAUUCCC | CUGACUGCUC | GCGGCUUGUG | GGGGCCACGC | 9000 |
| CAGAGCGCCC | CCGGCUGCGC | CUGGUCGACG | CCGACGACCC | CCUGCUGCGC | ACUGCCCCUG | 9060 |
| GACCCGGCGA | GGUGUGGGUC | ACGCCUGUCA | UAGGCUCUCA | GGCGCGCAAG | UGCGGACUCC | 9120 |
| ACAUACGCGC | UGGACCGUAC | GGCCAUGCUA | CCGUCGAAAU | GCCCGAGUGG | AUCCACGCCC | 9180 |
| ACACCACCAG | CGACCCCUGG | CAUCCACCGG | GCCCCUUGGG | GCUGAAGUUC | AAGACAGUUC | 9240 |
| GCCCGGUGGC | CCUGCCACGC | ACGUUAGCGC | CACCCCGCAA | UGUGCGUGUG | ACCGGGUGCU | 9300 |
| ACCAGUGCGG | UACCCCCGCG | CUGGUGGAAG | GCCUUGCCCC | CGGGGGAGGC | AAUUGCCAUC | 9360 |
| UCACCGUCAA | UGGCGAGGAC | CUCGGCGCCG | UCCCCCCUGG | GAAGUUCGUC | ACCGCCGCCC | 9420 |
| UCCUCAACAC | CCCCCCGCCC | UACCAAGUCA | GCUGCGGGGG | CGAGAGCGAU | CGCGCGACCG | 9480 |
| CGCGGGUCAU | CGACCCCGCC | GCGCAAUCGU | UUACCGGCGU | GGUGUAUGGC | ACACACACCA | 9540 |
| CUGCUGUGUC | GGAGACCCGG | CAGACCUGGG | CGGAGUGGGC | UGCUGCCCAU | UGGUGGCAGC | 9600 |
| UCACUCUGGG | CGCCAUUUGC | GCCCUCCCAC | UCGCUGGCUU | ACUCGCUUGC | UGUGCCAAAU | 9660 |
| GCUUGUACUA | CUUGCGCGGC | GCUAUAGCGC | CUCGCUAGUG | GGCCCCCGCG | CGAAACCCGC | 9720 |
| ACUAGGCCAC | UAGAUCCCCG | CACCUGUUGC | UGUAUAG | | | 9757 |

( 2 ) INFORMATION FOR SEQ ID NO:2:

( i ) SEQUENCE CHARACTERISTICS:
( A ) LENGTH: 2205 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: Nterminal ( v i ) ORIGINAL SOURCE:
( A ) ORGANISM: Rubella virus
( B ) STRAIN: Therien ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Glu | Lys | Leu | Leu | Asp | Glu | Val | Leu | Ala | Pro | Gly | Gly | Pro | Tyr | Asn |
| 1 | | | | 5 | | | | | 10 | | | | | 15 | |
| Leu | Thr | Val | Gly | Ser | Trp | Val | Arg | Asp | His | Val | Arg | Ser | Ile | Val | Glu |
| | | | 20 | | | | | 25 | | | | | 30 | | |
| Gly | Ala | Trp | Glu | Val | Arg | Asp | Val | Val | Thr | Ala | Ala | Gln | Lys | Arg | Ala |
| | | 35 | | | | | 40 | | | | | 45 | | | |
| Ile | Val | Ala | Val | Ile | Pro | Arg | Pro | Val | Phe | Thr | Gln | Met | Gln | Val | Ser |
| | 50 | | | | | 55 | | | | | 60 | | | | |
| Asp | His | Pro | Ala | Leu | His | Ala | Ile | Ser | Arg | Tyr | Thr | Arg | Arg | His | Trp |
| 65 | | | | | 70 | | | | | 75 | | | | | 80 |

-continued

| | | | | | | | | | | | | | | | |
|---|---|---|---|---|---|---|---|---|---|---|---|---|---|---|---|
| Ile | Glu | Trp | Gly | Pro | Lys | Glu | Ala | Leu | His | Val | Leu | Ile | Asp | Pro | Ser |
| | | | | 85 | | | | | 90 | | | | | 95 | |
| Pro | Gly | Leu | Leu | Arg | Glu | Val | Ala | Arg | Val | Glu | Arg | Arg | Trp | Val | Ala |
| | | | 100 | | | | | 105 | | | | | 110 | | |
| Leu | Cys | Leu | His | Arg | Thr | Ala | Arg | Lys | Leu | Ala | Thr | Ala | Leu | Ala | Glu |
| | | 115 | | | | | 120 | | | | | 125 | | | |
| Thr | Ala | Ser | Glu | Ala | Trp | His | Ala | Asp | Tyr | Val | Cys | Ala | Leu | Arg | Gly |
| | 130 | | | | | 135 | | | | | 140 | | | | |
| Ala | Pro | Ser | Gly | Pro | Phe | Tyr | Val | His | Pro | Glu | Asp | Val | Pro | His | Gly |
| 145 | | | | | 150 | | | | | 155 | | | | | 160 |
| Gly | Arg | Ala | Val | Ala | Asp | Arg | Cys | Leu | Leu | Tyr | Tyr | Thr | Pro | Met | Gln |
| | | | | 165 | | | | | 170 | | | | | 175 | |
| Met | Cys | Glu | Leu | Met | Arg | Thr | Ile | Asp | Ala | Thr | Leu | Leu | Val | Ala | Val |
| | | | 180 | | | | | 185 | | | | | 190 | | |
| Asp | Leu | Trp | Pro | Val | Ala | Leu | Ala | Ala | His | Val | Gly | Asp | Asp | Trp | Asp |
| | | 195 | | | | | 200 | | | | | 205 | | | |
| Asp | Leu | Gly | Ile | Ala | Trp | His | Leu | Asp | His | Asp | Gly | Gly | Cys | Pro | Ala |
| | 210 | | | | | 215 | | | | | 220 | | | | |
| Asp | Cys | Arg | Gly | Ala | Gly | Ala | Gly | Pro | Thr | Pro | Gly | Tyr | Thr | Arg | Pro |
| 225 | | | | | 230 | | | | | 235 | | | | | 240 |
| Cys | Thr | Thr | Arg | Ile | Tyr | Gln | Val | Leu | Pro | Asp | Thr | Ala | His | Pro | Gly |
| | | | | 245 | | | | | 250 | | | | | 255 | |
| Arg | Leu | Tyr | Arg | Cys | Gly | Pro | Arg | Leu | Trp | Thr | Arg | Asp | Cys | Ala | Val |
| | | | 260 | | | | | 265 | | | | | 270 | | |
| Ala | Glu | Leu | Ser | Trp | Glu | Val | Ala | Gln | His | Cys | Gly | His | Gln | Ala | Arg |
| | | 275 | | | | | 280 | | | | | 285 | | | |
| Val | Arg | Ala | Val | Arg | Cys | Thr | Leu | Pro | Ile | Arg | His | Val | Arg | Ser | Leu |
| | 290 | | | | | 295 | | | | | 300 | | | | |
| Gln | Pro | Ser | Ala | Arg | Val | Arg | Leu | Pro | Asp | Leu | Val | His | Leu | Ala | Glu |
| 305 | | | | | 310 | | | | | 315 | | | | | 320 |
| Val | Gly | Arg | Trp | Arg | Trp | Phe | Ser | Leu | Pro | Arg | Pro | Val | Phe | Gln | Arg |
| | | | | 325 | | | | | 330 | | | | | 335 | |
| Met | Leu | Ser | Tyr | Cys | Lys | Thr | Leu | Ser | Pro | Asp | Ala | Tyr | Tyr | Ser | Glu |
| | | | 340 | | | | | 345 | | | | | 350 | | |
| Arg | Val | Phe | Lys | Phe | Lys | Asn | Ala | Leu | Cys | His | Ser | Ile | Thr | Leu | Ala |
| | | 355 | | | | | 360 | | | | | 365 | | | |
| Gly | Asn | Val | Leu | Gln | Glu | Gly | Trp | Lys | Gly | Thr | Cys | Ala | Glu | Glu | Asp |
| | 370 | | | | | 375 | | | | | 380 | | | | |
| Ala | Leu | Cys | Ala | Tyr | Val | Ala | Phe | Arg | Ala | Trp | Gln | Ser | Asn | Ala | Arg |
| 385 | | | | | 390 | | | | | 395 | | | | | 400 |
| Leu | Ala | Gly | Ile | Met | Lys | Gly | Ala | Lys | Cys | Ala | Ala | Asp | Ser | Leu | Ser |
| | | | | 405 | | | | | 410 | | | | | 415 | |
| Val | Ala | Gly | Trp | Leu | Asp | Thr | Ile | Trp | Asp | Ala | Ile | Lys | Arg | Phe | Leu |
| | | | 420 | | | | | 425 | | | | | 430 | | |
| Gly | Ser | Val | Pro | Leu | Ala | Glu | Arg | Met | Glu | Glu | Trp | Glu | Gln | Asp | Ala |
| | | 435 | | | | | 440 | | | | | 445 | | | |
| Ala | Val | Ala | Ala | Phe | Asp | Arg | Gly | Pro | Leu | Glu | Asp | Gly | Gly | Arg | His |
| | 450 | | | | | 455 | | | | | 460 | | | | |
| Leu | Asp | Thr | Val | Gln | Pro | Pro | Lys | Ser | Pro | Pro | Arg | Pro | Glu | Ile | Ala |
| 465 | | | | | 470 | | | | | 475 | | | | | 480 |
| Ala | Thr | Trp | Ile | Val | His | Ala | Ala | Ser | Glu | Asp | Arg | His | Cys | Ala | Cys |
| | | | | 485 | | | | | 490 | | | | | 495 | |
| Ala | Pro | Arg | Cys | Asp | Val | Pro | Arg | Glu | Arg | Pro | Ser | Ala | Pro | Ala | Gly |
| | | | 500 | | | | | 505 | | | | | 510 | | |
| Gln | Pro | Asp | Asp | Glu | Ala | Leu | Ile | Pro | Pro | Trp | Leu | Phe | Ala | Glu | Arg |

-continued

```
            515                     520                     525

Arg Ala Leu Arg Cys Arg Glu Trp Asp Phe Glu Ala Leu Arg Ala Arg
    530                 535                 540

Ala Asp Thr Ala Ala Ala Pro Ala Pro Pro Ala Pro Arg Pro Ala Arg
545                 550                 555                 560

Tyr Pro Thr Val Leu Tyr Arg His Pro Ala His His Gly Pro Trp Leu
                565                 570                 575

Thr Leu Asp Glu Pro Gly Glu Ala Asp Ala Ala Leu Val Leu Cys Asp
            580                 585                 590

Pro Leu Gly Gln Pro Leu Arg Gly Pro Glu Arg His Phe Ala Ala Gly
        595                 600                 605

Ala His Met Cys Ala Gln Ala Arg Gly Leu Gln Ala Phe Val Arg Val
    610                 615                 620

Val Pro Pro Pro Glu Arg Pro Trp Ala Asp Gly Gly Ala Arg Ala Trp
625                 630                 635                 640

Ala Lys Phe Phe Arg Gly Cys Ala Trp Ala Gln Arg Leu Leu Gly Glu
                645                 650                 655

Pro Ala Val Met His Leu Pro Tyr Thr Asp Gly Asp Val Pro Gln Leu
            660                 665                 670

Ile Ala Leu Ala Leu Arg Thr Leu Ala Gln Gln Gly Ala Ala Leu Ala
        675                 680                 685

Leu Ser Val Arg Asp Leu Pro Gly Gly Ala Ala Phe Asp Ala Asn Ala
    690                 695                 700

Val Thr Ala Ala Val Arg Ala Gly Pro Arg Gln Ser Ala Ala Ala Ser
705                 710                 715                 720

Pro Pro Pro Gly Asp Pro Pro Pro Pro Arg Arg Ala Arg Arg Ser Gln
                725                 730                 735

Arg His Ser Asp Ala Arg Gly Thr Pro Pro Pro Ala Pro Ala Arg Asp
            740                 745                 750

Pro Pro Pro Pro Ala Pro Ser Pro Pro Ala Pro Pro Arg Ala Gly Asp
        755                 760                 765

Pro Val Pro Pro Ile Pro Ala Gly Pro Ala Asp Arg Ala Arg Asp Ala
    770                 775                 780

Glu Leu Glu Val Ala Cys Glu Pro Ser Gly Pro Pro Thr Ser Thr Arg
785                 790                 795                 800

Ala Asp Pro Asp Ser Asp Ile Val Glu Ser Tyr Ala Arg Ala Ala Gly
                805                 810                 815

Pro Val His Leu Arg Val Arg Asp Ile Met Asp Pro Pro Pro Gly Cys
            820                 825                 830

Lys Val Val Val Asn Ala Ala Asn Glu Gly Leu Leu Ala Gly Ser Gly
        835                 840                 845

Val Cys Gly Ala Ile Phe Ala Asn Ala Thr Ala Ala Leu Ala Ala Asn
    850                 855                 860

Cys Arg Arg Leu Ala Pro Cys Pro Thr Gly Glu Ala Val Ala Thr Pro
865                 870                 875                 880

Gly His Gly Cys Gly Tyr Thr His Ile Ile His Ala Val Ala Pro Arg
                885                 890                 895

Arg Pro Arg Asp Pro Ala Ala Leu Glu Glu Gly Glu Ala Leu Leu Glu
            900                 905                 910

Arg Ala Tyr Arg Ser Ile Val Ala Leu Ala Ala Ala Arg Arg Trp Ala
        915                 920                 925

Cys Val Ala Cys Pro Leu Leu Gly Ala Gly Val Tyr Gly Trp Ser Ala
    930                 935                 940

Ala Glu Ser Leu Arg Ala Ala Leu Ala Ala Thr Arg Thr Glu Pro Val
945                 950                 955                 960
```

-continued

Glu Arg Val Ser Leu His Ile Cys His Pro Asp Arg Ala Thr Leu Thr
965 970 975

His Ala Ser Val Leu Val Gly Ala Gly Leu Ala Ala Arg Arg Val Ser
980 985 990

Pro Pro Pro Thr Glu Pro Leu Ala Ser Cys Pro Ala Gly Asp Pro Gly
995 1000 1005

Arg Pro Ala Gln Arg Ser Ala Ser Pro Pro Ala Thr Pro Leu Gly Asp
1010 1015 1020

Ala Thr Ala Pro Glu Pro Arg Gly Cys Gln Gly Cys Glu Leu Cys Arg
1025 1030 1035 1040

Tyr Thr Arg Val Thr Asn Asp Arg Ala Tyr Val Asn Leu Trp Leu Glu
1045 1050 1055

Arg Asp Arg Gly Ala Thr Ser Trp Ala Met Arg Ile Pro Glu Val Val
1060 1065 1070

Val Tyr Gly Pro Glu His Leu Ala Thr His Phe Pro Leu Asn His Tyr
1075 1080 1085

Ser Val Leu Lys Pro Ala Glu Val Arg Pro Pro Arg Gly Met Cys Gly
1090 1095 1100

Ser Asp Met Trp Arg Cys Arg Gly Trp His Gly Met Pro Gln Val Arg
1105 1110 1115 1120

Cys Thr Pro Ser Asn Ala His Ala Ala Leu Cys Arg Thr Gly Val Pro
1125 1130 1135

Pro Arg Ala Ser Thr Arg Gly Gly Glu Leu Asp Pro Asn Thr Cys Trp
1140 1145 1150

Leu Arg Ala Ala Ala Asn Val Ala Gln Ala Ala Arg Ala Cys Gly Ala
1155 1160 1165

Tyr Thr Ser Ala Gly Cys Pro Lys Cys Ala Tyr Gly Arg Ala Leu Ser
1170 1175 1180

Glu Ala Arg Thr His Glu Asp Phe Ala Ala Leu Ser Gln Arg Trp Ser
1185 1190 1195 1200

Ala Ser His Ala Asp Ala Ser Pro Asp Gly Thr Gly Asp Pro Leu Asp
1205 1210 1215

Pro Leu Met Glu Thr Val Gly Cys Ala Cys Ser Arg Val Trp Val Gly
1220 1225 1230

Ser Glu His Glu Ala Pro Pro Asp His Leu Leu Val Ser Leu His Arg
1235 1240 1245

Ala Pro Asn Gly Pro Trp Gly Val Val Leu Glu Val Arg Ala Arg Pro
1250 1255 1260

Glu Gly Gly Asn Pro Thr Gly His Phe Val Cys Ala Val Gly Gly Gly
1265 1270 1275 1280

Pro Arg Arg Val Ser Asp Arg Pro His Leu Trp Leu Ala Val Pro Leu
1285 1290 1295

Ser Arg Gly Gly Gly Thr Cys Ala Ala Thr Asp Glu Gly Leu Ala Gln
1300 1305 1310

Ala Tyr Tyr Asp Asp Leu Glu Val Arg Arg Leu Gly Asp Asp Ala Met
1315 1320 1325

Ala Arg Ala Ala Leu Ala Ser Val Gln Arg Pro Arg Lys Gly Pro Tyr
1330 1335 1340

Asn Ile Arg Val Trp Asn Met Ala Ala Gly Ala Gly Lys Thr Thr Arg
1345 1350 1355 1360

Ile Leu Ala Ala Phe Thr Arg Glu Asp Leu Tyr Val Cys Pro Thr Asn
1365 1370 1375

Ala Leu Leu His Glu Ile Gln Ala Lys Leu Arg Ala Arg Asp Ile Asp
1380 1385 1390

-continued

Ile Lys Asn Ala Ala Thr Tyr Glu Arg Arg Leu Thr Lys Pro Leu Ala
1395 1400 1405

Ala Tyr Arg Arg Ile Tyr Ile Asp Glu Ala Phe Thr Leu Gly Gly Glu
1410 1415 1420

Tyr Cys Ala Phe Val Ala Ser Gln Thr Thr Ala Glu Val Ile Cys Val
1425 1430 1435 1440

Gly Asp Arg Asp Gln Cys Gly Pro His Tyr Ala Asn Asn Cys Arg Thr
1445 1450 1455

Pro Val Pro Asp Arg Trp Pro Thr Glu Arg Ser Arg His Thr Trp Arg
1460 1465 1470

Phe Pro Asp Cys Trp Ala Ala Arg Leu Arg Ala Gly Leu Asp Tyr Asp
1475 1480 1485

Ile Glu Gly Glu Arg Thr Gly Thr Phe Ala Cys Asn Leu Trp Asp Gly
1490 1495 1500

Arg Gln Val Asp Leu His Leu Ala Phe Ser Arg Glu Thr Val Arg Arg
1505 1510 1515 1520

Leu His Glu Ala Gly Ile Arg Ala Tyr Thr Val Arg Glu Ala Gln Gly
1525 1530 1535

Met Ser Val Gly Thr Ala Cys Ile His Val Gly Arg Asp Gly Thr Asp
1540 1545 1550

Val Ala Leu Ala Leu Thr Arg Asp Leu Ala Ile Val Ser Leu Thr Arg
1555 1560 1565

Ala Ser Asp Ala Leu Tyr Leu His Glu Leu Glu Asp Gly Ser Leu Arg
1570 1575 1580

Ala Ala Gly Leu Ser Ala Phe Leu Asp Ala Gly Ala Leu Ala Glu Leu
1585 1590 1595 1600

Lys Glu Val Pro Ala Gly Ile Asp Arg Val Val Ala Val Glu Gln Ala
1605 1610 1615

Pro Pro Pro Leu Pro Pro Ala Asp Gly Ile Pro Glu Ala Gln Asp Val
1620 1625 1630

Pro Pro Phe Cys Pro Arg Thr Leu Glu Glu Leu Val Phe Gly Arg Ala
1635 1640 1645

Gly His Pro His Tyr Ala Asp Leu Asn Arg Val Thr Glu Gly Glu Arg
1650 1655 1660

Glu Val Arg Tyr Met Arg Ile Ser Arg His Leu Leu Asn Lys Asn His
1665 1670 1675 1680

Thr Glu Met Pro Gly Thr Glu Arg Val Leu Ser Ala Val Cys Ala Val
1685 1690 1695

Arg Arg Tyr Arg Ala Gly Glu Asp Gly Ser Thr Leu Arg Thr Ala Val
1700 1705 1710

Ala Arg Gln His Pro Arg Pro Phe Arg Gln Ile Pro Pro Pro Arg Val
1715 1720 1725

Thr Ala Gly Val Ala Gln Glu Trp Arg Met Thr Tyr Leu Arg Glu Arg
1730 1735 1740

Ile Asp Leu Thr Asp Val Tyr Thr Gln Met Gly Val Ala Ala Arg Glu
1745 1750 1755 1760

Leu Thr Asp Arg Tyr Ala Arg Arg Tyr Pro Glu Ile Phe Ala Gly Met
1765 1770 1775

Cys Thr Ala Gln Ser Leu Ser Val Pro Ala Phe Leu Lys Ala Thr Leu
1780 1785 1790

Lys Cys Val Asp Ala Ala Leu Gly Pro Arg Asp Thr Glu Asp Cys His
1795 1800 1805

Ala Ala Gln Gly Lys Ala Gly Leu Glu Ile Arg Ala Trp Ala Lys Glu
1810 1815 1820

Trp Val Gln Val Met Ser Pro His Phe Arg Ala Ile Gln Lys Ile Ile

-continued

```
1825                    1830                    1835                    1840

Met Arg Ala Leu Arg Pro Gln Phe Leu Val Ala Ala Gly His Thr Glu
                    1845                    1850                    1855

Pro Glu Val Asp Ala Trp Trp Gln Ala His Tyr Thr Thr Asn Ala Ile
                1860                    1865                    1870

Glu Val Asp Phe Thr Glu Phe Asp Met Asn Gln Thr Leu Ala Thr Arg
            1875                    1880                    1885

Asp Val Glu Leu Glu Ile Ser Ala Ala Leu Leu Gly Leu Pro Cys Ala
        1890                    1895                    1900

Glu Asp Tyr Arg Ala Leu Arg Ala Gly Ser Tyr Cys Thr Leu Arg Glu
1905                    1910                    1915                    1920

Leu Gly Ser Thr Glu Thr Gly Cys Glu Arg Thr Ser Gly Glu Pro Ala
                    1925                    1930                    1935

Thr Leu Leu His Asn Thr Thr Val Ala Met Cys Met Ala Met Arg Met
                1940                    1945                    1950

Val Pro Lys Gly Val Arg Trp Ala Gly Ile Phe Gln Gly Asp Asp Met
            1955                    1960                    1965

Val Ile Phe Leu Pro Glu Gly Ala Arg Ser Ala Ala Leu Lys Trp Thr
        1970                    1975                    1980

Pro Ala Glu Val Gly Leu Phe Gly Phe His Ile Pro Val Lys His Val
1985                    1990                    1995                    2000

Ser Thr Pro Thr Pro Ser Phe Cys Gly His Val Gly Thr Ala Ala Gly
                    2005                    2010                    2015

Leu Phe His Asp Val Met His Gln Ala Ile Lys Val Leu Cys Arg Arg
                2020                    2025                    2030

Phe Asp Pro Asp Val Leu Glu Glu Gln Gln Val Ala Leu Leu Asp Arg
            2035                    2040                    2045

Leu Arg Gly Val Tyr Ala Ala Leu Pro Asp Thr Val Ala Ala Asn Ala
        2050                    2055                    2060

Ala Tyr Tyr Asp Tyr Ser Ala Glu Arg Val Leu Ala Ile Val Arg Glu
2065                    2070                    2075                    2080

Leu Thr Ala Tyr Ala Gly Ala Arg Pro Arg Pro Pro Gly His His Arg
                    2085                    2090                    2095

Arg Ala Arg Gly Asp Ser Asp Pro Leu Arg Ala Arg Gln Ser Pro Arg
                2100                    2105                    2110

Arg Arg Leu Thr Pro Leu Tyr Val Gly Pro Leu Ile Leu Pro Thr Leu
            2115                    2120                    2125

Thr Arg Ser Ser Pro Thr Val Val Ser Pro His Leu Val Gly Thr Gln
        2130                    2135                    2140

Leu Leu Pro Phe Gly Arg Ala Pro Gly Cys Pro Asn Gly Phe Tyr Tyr
2145                    2150                    2155                    2160

Pro His His His Gly Gly Pro Pro Glu Gly Pro Arg Gly Thr Ile Pro
                    2165                    2170                    2175

Arg Pro Ala Arg Gly Thr Arg Arg Arg Arg Leu Ala Asx Ala Pro Ala
                2180                    2185                    2190

Ala Ala Ala Ala Thr Ala Arg Leu Gln His Leu Arg Arg
            2195                    2200                    2205
```

( 2 ) INFORMATION FOR SEQ ID NO:3:

( i ) SEQUENCE CHARACTERISTICS:
( A ) LENGTH: 1063 amino acids
( B ) TYPE: amino acid
( C ) STRANDEDNESS: single
( D ) TOPOLOGY: linear ( i i ) MOLECULE TYPE: peptide -continued ( i i i ) HYPOTHETICAL: NO ( i v ) ANTI-SENSE: NO ( v ) FRAGMENT TYPE: Cterminal ( v i ) ORIGINAL SOURCE:
( A ) ORGANISM: Rubella virus
( B ) STRAIN: Therien ( x i ) SEQUENCE DESCRIPTION: SEQ ID NO:3:

Met Ala Ser Thr Thr Pro Ile Thr Met Glu Asp Leu Gln Lys Ala Leu
1 5 10 15

Glu Ala Gln Ser Arg Ala Leu Arg Ala Glu Leu Ala Ala Gly Ala Ser
20 25 30

Gln Ser Arg Arg Pro Arg Pro Pro Arg Gln Arg Asp Ser Ser Thr Ser
35 40 45

Gly Asp Asp Ser Gly Arg Asp Ser Gly Gly Pro Arg Arg Arg Arg Gly
50 55 60

Asn Arg Gly Arg Gly Gln Arg Arg Asp Trp Ser Arg Ala Pro Pro Pro
65 70 75 80

Pro Glu Glu Arg Gln Glu Thr Arg Ser Gln Thr Pro Ala Pro Lys Pro
85 90 95

Ser Arg Ala Pro Pro Gln Gln Pro Gln Pro Pro Arg Met Gln Thr Gly
100 105 110

Arg Gly Gly Ser Ala Pro Arg Pro Glu Leu Gly Pro Pro Thr Asn Pro
115 120 125

Phe Gln Ala Ala Val Ala Arg Gly Leu Arg Pro Pro Leu His Asp Pro
130 135 140

Asp Thr Glu Ala Pro Thr Glu Ala Cys Val Thr Ser Trp Leu Trp Ser
145 150 155 160

Glu Gly Glu Gly Ala Val Phe Tyr Arg Val Asp Leu His Phe Thr Asn
165 170 175

Leu Gly Thr Pro Pro Leu Asp Glu Asp Gly Arg Trp Asp Pro Ala Leu
180 185 190

Met Tyr Asn Pro Cys Gly Pro Glu Pro Pro Ala His Val Val Arg Ala
195 200 205

Tyr Asn Gln Pro Ala Gly Asp Val Arg Gly Val Trp Gly Lys Gly Glu
210 215 220

Arg Thr Tyr Ala Glu Gln Asp Phe Arg Val Gly Gly Thr Arg Trp His
225 230 235 240

Arg Leu Leu Arg Met Pro Val Arg Gly Leu Asp Gly Asp Ser Ala Pro
245 250 255

Leu Pro Pro His Thr Thr Glu Arg Ile Glu Thr Arg Ser Ala Arg His
260 265 270

Pro Trp Arg Ile Arg Phe Gly Ala Pro Gln Ala Phe Leu Ala Gly Leu
275 280 285

Leu Leu Ala Thr Val Ala Val Gly Thr Ala Arg Ala Gly Leu Gln Pro
290 295 300

Arg Ala Asp Met Ala Ala Pro Pro Thr Leu Pro Gln Pro Pro Cys Ala
305 310 315 320

His Gly Gln His Tyr Gly His His His His Gln Leu Pro Phe Leu Gly
325 330 335

His Asp Gly His His Gly Gly Thr Leu Arg Val Gly Gln His Tyr Arg
340 345 350

Asn Ala Ser Asp Val Leu Pro Gly His Trp Leu Gln Gly Gly Trp Gly
355 360 365

Cys Tyr Asn Leu Ser Asp Trp His Gln Gly Thr His Val Cys His Thr

-continued 370 375 380

Lys His Met Asp Phe Trp Cys Val Glu His Asp Arg Pro Pro Pro Ala
385 390 395 400

Thr Pro Thr Pro Leu Thr Thr Ala Ala Asn Ser Thr Thr Ala Ala Thr
405 410 415

Pro Ala Thr Ala Pro Ala Pro Cys His Ala Gly Leu Asn Asp Ser Cys
420 425 430

Gly Gly Phe Leu Ser Gly Cys Gly Pro Met Arg Leu Arg His Gly Ala
435 440 445

Asp Thr Arg Cys Gly Arg Leu Ile Cys Gly Leu Ser Thr Thr Ala Gln
450 455 460

Tyr Pro Pro Thr Arg Phe Gly Cys Ala Met Arg Trp Gly Leu Pro Pro
465 470 475 480

Trp Glu Leu Val Val Leu Thr Ala Arg Pro Glu Asp Gly Trp Thr Cys
485 490 495

Arg Gly Val Pro Ala His Pro Gly Ala Arg Cys Pro Glu Leu Val Ser
500 505 510

Pro Met Gly Arg Ala Thr Cys Ser Pro Ala Ser Ala Leu Trp Leu Ala
515 520 525

Thr Ala Asn Ala Leu Ser Leu Asp His Ala Leu Ala Ala Phe Val Leu
530 535 540

Leu Val Pro Trp Val Leu Ile Phe Met Val Cys Arg Arg Ala Cys Arg
545 550 555 560

Arg Arg Gly Ala Ala Ala Ala Leu Thr Ala Val Val Leu Gln Gly Tyr
565 570 575

Asn Pro Pro Ala Tyr Gly Glu Glu Ala Phe Thr Tyr Leu Cys Thr Ala
580 585 590

Pro Gly Cys Ala Thr Gln Ala Pro Val Pro Val Arg Leu Ala Gly Val
595 600 605

Arg Phe Glu Ser Lys Ile Val Asp Gly Gly Cys Phe Ala Pro Trp Asp
610 615 620

Leu Glu Ala Thr Gly Ala Cys Ile Cys Glu Ile Pro Thr Asp Val Ser
625 630 635 640

Cys Glu Gly Leu Gly Ala Trp Val Pro Ala Ala Pro Cys Ala Arg Ile
645 650 655

Trp Asn Gly Thr Gln Arg Ala Cys Thr Phe Trp Ala Val Asn Ala Tyr
660 665 670

Ser Ser Gly Gly Tyr Ala Gln Leu Ala Ser Tyr Phe Asn Pro Gly Gly
675 680 685

Ser Tyr Tyr Lys Gln Tyr His Pro Thr Ala Cys Glu Val Glu Pro Ala
690 695 700

Phe Gly His Ser Asp Ala Ala Cys Trp Gly Phe Pro Thr Asp Thr Val
705 710 715 720

Met Ser Val Phe Ala Leu Ala Ser Tyr Val Gln His Pro His Lys Thr
725 730 735

Val Arg Val Lys Phe His Thr Glu Thr Arg Thr Val Trp Gln Leu Ser
740 745 750

Val Ala Gly Val Ser Cys Asn Val Thr Thr Glu His Pro Phe Cys Asn
755 760 765

Thr Pro His Gly Gln Leu Glu Val Gln Val Pro Pro Asp Pro Gly Asp
770 775 780

Leu Val Glu Tyr Ile Met Asn Tyr Thr Gly Asn Gln Gln Ser Arg Trp
785 790 795 800

Gly Leu Gly Ser Pro Asn Cys His Gly Pro Asp Trp Ala Ser Pro Val
805 810 815

-continued

Cys Gln Arg His Ser Pro Asp Cys Ser Arg Leu Val Gly Ala Thr Pro
820 825 830

Glu Arg Pro Arg Leu Arg Leu Val Asp Ala Asp Asp Pro Leu Leu Arg
835 840 845

Thr Ala Pro Gly Pro Gly Glu Val Met Val Thr Pro Val Ile Gly Ser
850 855 860

Gln Ala Arg Lys Cys Gly Leu His Ile Arg Ala Gly Pro Tyr Gly His
865 870 875 880

Ala Thr Val Glu Met Pro Glu Trp Ile His Ala His Thr Thr Ser Asp
885 890 895

Pro Trp His Pro Pro Gly Pro Leu Gly Leu Lys Phe Lys Thr Val Arg
900 905 910

Pro Val Ala Leu Pro Arg Thr Leu Ala Pro Pro Arg Asn Val Arg Val
915 920 925

Thr Gly Cys Tyr Gln Cys Gly Thr Pro Ala Leu Val Glu Gly Leu Ala
930 935 940

Pro Gly Gly Gly Asn Cys His Leu Thr Val Asn Gly Glu Asp Leu Gly
945 950 955 960

Ala Val Pro Pro Gly Lys Phe Val Thr Ala Ala Leu Leu Asn Thr Pro
965 970 975

Pro Pro Tyr Gln Val Ser Cys Gly Gly Glu Ser Asp Arg Ala Thr Ala
980 985 990

Arg Val Ile Asp Pro Ala Ala Gln Ser Phe Thr Gly Val Val Tyr Gly
995 1000 1005

Thr His Thr Thr Ala Val Ser Glu Thr Arg Gln Thr Trp Ala Glu Trp
1010 1015 1020

Ala Ala Ala His Trp Trp Gln Leu Thr Leu Gly Ala Ile Cys Ala Leu
1025 1030 1035 1040

Pro Leu Ala Gly Leu Leu Ala Cys Cys Ala Lys Cys Leu Tyr Tyr Leu
1045 1050 1055

Arg Gly Ala Ile Ala Pro Arg
1060

( 2 ) INFORMATION FOR SEQ ID NO:4:

( i ) SEQUENCE CHARACTERISTICS:
( A ) LENGTH: 17
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:4:

TGGTCTCTTA CCCAACT 17

( 2 ) INFORMATION FOR SEQ ID NO:5:

( i ) SEQUENCE CHARACTERISTICS:
( A ) LENGTH: 45
( B ) TYPE: nucleic acid
( C ) STRANDEDNESS: single
( D ) TOPOLOGY: linear ( i i ) MOLECULE TYPE: cDNA to genomic RNA -continued ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:5:

AGCTACTAGT CTAAGCTTTC GGACCTCGCT TAGGACTCCC ATTCC 45

( 2 ) INFORMATION FOR SEQ ID NO:6:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: complementary to nucleotides 5-45 of SEQ ID NO: 5

( i i i ) HYPOTHETICAL: NO ( i v ) ANTI-SENSE: YES ( v i ) ORIGINAL SOURCE:
( A ) ORGANISM: Rubella virus
( B ) STRAIN: Therien ( x i ) SEQUENCE DESCRIPTION: SEQ ID NO:6:

CATGGGAATG GGAGTCCTAA GCGAGGTCCG AAAGCTTAGA CTAGT 45

( 2 ) INFORMATION FOR SEQ ID NO:7:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:7:

TTCGAAGCTT ATTTAGGTCA CACTATAGCA TGGAAGCTAT CGGACCTC 48

( 2 ) INFORMATION FOR SEQ ID NO:8:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:8:

-continued

TGGTCTCTTA CCCAACT 17

( 2 ) INFORMATION FOR SEQ ID NO:9:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:9:

GATGCATCCC TATAGTGAGT CGTATTAG 28

( 2 ) INFORMATION FOR SEQ ID NO:10:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:10:

AATTCTAATA CGACTCACTA TAGGGATGCA TCTGCA 36

( 2 ) INFORMATION FOR SEQ ID NO:11:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:11:

AATGCCCGAG TGGATCCA 18

( 2 ) INFORMATION FOR SEQ ID NO:12:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA to genomic RNA -continued ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:12:

ACGTGCATGC CTGCAGTTTT TTTTTTTTTT TTTTTT 36

( 2 ) INFORMATION FOR SEQ ID NO:13:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: cDNA to genomic RNA ( i i i ) HYPOTHETICAL: NO ( i v ) ANTI-SENSE: NO ( v i ) ORIGINAL SOURCE:
( A ) ORGANISM: Rubella virus
( B ) STRAIN: Therien ( x i ) SEQUENCE DESCRIPTION: SEQ ID NO:13:

AAGCTTATTT AGGTGACACT ATAGNNATGG AAGCTATCGG ACCTCGCTT 49

DNA ENCODING INFECTIOUS RUBELLA VIRUS

This is a continuation of application U.S. Ser. No. 07/722,334, filed on Jun. 28, 1991, now abandoned.

The present invention relates to the field of molecular virology and more particularly to construction of a modified recombinant rubella virus vaccine.

The U.S. Government has rights in this invention arising out of National Institutes of Health (NIAID) grant numbers AI21389 and AI00923.

BACKGROUND OF THE INVENTION

Rubella virus is a major human pathogen. Infection with rubella virus can cause serious birth defects and chronic disease. The number of cases of rubella and congenital rubella syndrome has increased greatly from 1989 to 1990, indicating a current rubella epidemic.

Rubella was first described in the eighteenth century in Germany. The symptoms of a rash and mild fever were similar to those of measles, so the disease was given the name German measles. The name "rubella" was coined in 1814 when physicians realized that the disease was unique and was not merely a variant of scarlatina (scarlet fever) or rubeola (measles).

Rubella is a relatively harmless disease in young children. However, during the first trimester of pregnancy, rubella virus infection can cause fetal death. If the fetus survives, it may be born deaf or have cataracts, cardiac abnormalities, microcephaly, motor deficits or other congenital anomalies. The infant may also be born with thrombocytopenic purpura, hepatosplenomegaly, icterus, anemia, and low birth weight. The presence of one or more of these defects has been termed "congenital rubella syndrome" or CRS.

The rubella virus was isolated in 1962 at the beginning of a worldwide rubella epidemic which lasted from 1962 to 1965. This epidemic peaked in the United States in 1964, resulting in the birth of approximately 20,000 infants exhibiting congenital rubella syndrome.

Scientists began development of an effective vaccine against the rubella virus during the rubella epidemic. Effective attenuated vaccines became available in the late 1960's and are still used today. These attenuated vaccines are live viruses that have been passaged to reduce their virulence. Attenuated vaccines produce immunity, but can cause disease. Protection is believed to persist for at least 15 years after inoculation with the attenuated rubella vaccine.

Various vaccination schedules have been set up in different parts of the world to eliminate rubella infection, especially of the human fetus. The rubella immunization program established in Great Britain requires vaccination of all girls between the ages of 10 and 14. The United States immunization program vaccinates infants at approximately 15 months and requires a certificate of vaccination prior to attending school. The United States program is designed to eradicate the disease among the population that is most responsible for transmission of rubella, whereas the program of Great Britain seeks to achieve complete protection for those at risk for pregnancy. One disadvantage to the United States program is that protection against rubella may dissipate at the very time when immunity is most needed, namely, during the child-bearing years.

Vaccination of women of child-bearing age having undetectable antibody titers is recommended in both the United States and Great Britain. However, there are several risks to this procedure. First, there is a risk that these women may be pregnant and not be aware of their pregnancy, or they may become pregnant within a few months following immunization. Vaccination against rubella is contraindicated in pregnant women because the live virus in the vaccine can cross the placenta and infect the fetus. Pregnant women who have not previously been infected with the rubella virus or who have not been vaccinated prior to becoming pregnant are advised to refrain from becoming vaccinated during their pregnancy. These women are therefore at risk for contracting rubella by coming in contact with infectious persons, including those recently vaccinated with the attenuated vaccine.

Vaccination of older women has been associated with chronic arthritis and neurological symptoms. Scientists believe that these symptoms may be due to the persistent nature of the attenuated rubella virus in the currently available vaccines.

Rubella virus is the sole member of the rubivirus genus of the Togavirus family. Compared to other viruses, very little is known about the molecular biology of the rubella virus. The rubella virion consists of single-stranded RNA encapsidated in an icosahedral nucleocapsid surrounded by a lipid envelope. Multiple copies of a viral protein, designated the C protein (Mr=32,000–38,000 daltons), make up the nucleocapsid. Two types of viral glycoprotein, designated E1 and E2 (Mr=53,000–58,000 daltons and 42,000–48,000 daltons, respectively), are embedded in the envelope, as reported by Waxham, M. N. and Wolinsky, J. S., *Virology* 126:194–203 (1983). The E2 glycoprotein has been further subdivided into two subgroups, designated E2a and E2b, by their ability to migrate differently when resolved by polyacrylamide gel electrophoresis, as described by Oker-Blom, C., et al., *J. Virol.* 46:964–973 (1983). E1 is the viral hemagglutinin. Neutralizing epitopes have been found on both E1 and E2 by Waxham, M. N. and Wolinsky, J. S., *Virology* 143:153–165 (1985) and Green, K. Y., and Dorsett, P. H., *J. Virol.*, 57:893–898 (1986).

The rubella virus genomic RNA is of positive polarity and is capped and polyadenylated. In infected cells, a second positive polarity RNA strand is synthesized to serve as messenger RNA for translation of structural proteins. This second strand is the first 3327 nucleotides beginning from the 3′ end of the genomic RNA. The structural proteins are proteolytically processed from a polyprotein precursor during translation. The order of these proteins in the polyprotein is $NH_2$-C-E2-E1-COOH, as reported by Oker-Blom, C., et al. (1983). The gene order for rubella virus structural protein is $NH_2$-C-E2-E1-COOH, Oker-Blom, C. *J. Virol.* 51:354–358 (1984).

Recombinant vaccines are based on live microorganisms which have been genetically manipulated so that they are not pathogenic, but result in immunity against the virulent organism. Recombinant vaccines can only cause disease if a rare genetic mutation or recombinant event occurs which allows the microorganism to revert to wild type. A recombinant vaccine is generally safer and more effective than an attenuated vaccine because the engineered mutations remove or inactivate only specific portions of the genome, whereas attenuated vaccines contain random mutations. In order to develop a recombinant vaccine, one must first have the nucleic acid sequence of the entire viral genome, including both the information required for infection and at least limited replication of the virus, and for antigenicity. Once the entire sequence has been determined, a cDNA clone can be produced that is infectious and can be modified to be non-virulent.

An infectious cDNA clone is a complete DNA copy of an RNA virus genome contained in a vector, such as a plasmid, from which RNA transcripts of the genome can be synthesized in vitro. In the case of positive-polarity RNA viruses such as rubella, such transcripts are infectious when transfected into cells. The development of an infectious clone is a landmark event in the molecular biology of any RNA virus. Although Rice et al., *Virology* 61:3809–3819 (1987), have recently developed an infectious clone for the Sindbis virus, no infectious clones have yet been developed for the rubella virus.

Scientists have made many attempts over the past few years to sequence the rubella virus genomic RNA, but have only succeeded in sequencing the genes for the structural proteins and a small section of the 3′ end of the non-structural virus genome. Frey, et al., *Virology* 154:228–232 (1986), reported the sequence of the region of the rubella virus genome encoding the glycoprotein E1. These results were confirmed by Nakhasi, et al., *J. Biol. Chem.* 261:16616–16621 (1986). Clark, et al., *Nucleic Acids Res.* 15:3041–3057 (1987), reported the sequence of the subgenomic mRNA of the rubella virus encoding the structural proteins E1, E2 and C. Vidgren, et al., *J. gen. Virol.* 68:2347–2357 (1987), reported the sequencing of the genes for glycoproteins E1 and E2. Takkinen, et al., *J. gen Virol.* 69:603–612 (1988), described the isolation of the sequence encoding the virus capsid protein C. Frey and Marr, *Gene* 62:85–99 (1988), described the sequence of the structural proteins C and E2 as well as the carboxyl terminus of a portion of the non-structural virus genome.

It is clear that there remains a strong need to have the complete sequence of the rubella virus RNA genome. Once the sequence is known, an infectious cDNA clone of the rubella virus genome can be developed and used to design a rubella vaccine that can be safely administered to pregnant and older women without risk of birth defects, autoimmune disease or neurologic symptoms.

It is therefore an object of the present invention to provide the entire sequence of the rubella virus genomic RNA.

It is a further object of the present invention to provide an infectious cDNA clone of the rubella virus genomic RNA.

It is a still further object of the present invention to provide a recombinant attenuated rubella vaccine derived from a non-pathogenic infectious cDNA clone that can be safely administered to pregnant and older women.

It is another object of the present invention to provide a combined recombinant attenuated vaccine effective against rubella and one or more other viruses.

SUMMARY OF THE INVENTION

The present invention is the entire sequence of the rubella virus genome including the 5248 nucleotides at the 5′ terminus encoding non-structural proteins which are critical to infection by the virus, an infectious cDNA clone containing the sequence, and recombinant vaccines against the rubella virus based on the recombinant clone in a pharmaceutically acceptable carrier for administration to a patient.

The recombinant rubella vaccine is prepared by transcribing RNA from a plasmid containing a non-pathogenic, infectious cDNA clone, infecting culture cells with the RNA, replicating the RNA to produce recombinant virus, and combining the virus with a pharmaceutically acceptable carrier, which is then administered to people to be vaccinated, using a schedule and amount demonstrated to be efficacious with other attenuated rubella vaccines. In a second embodiment of this vaccine, the vaccine contains/immunogenic epitopes against other viruses, providing a means for immunizing against more than one virus in a single vaccine.

DETAILED DESCRIPTION OF THE INVENTION

Figure 1:
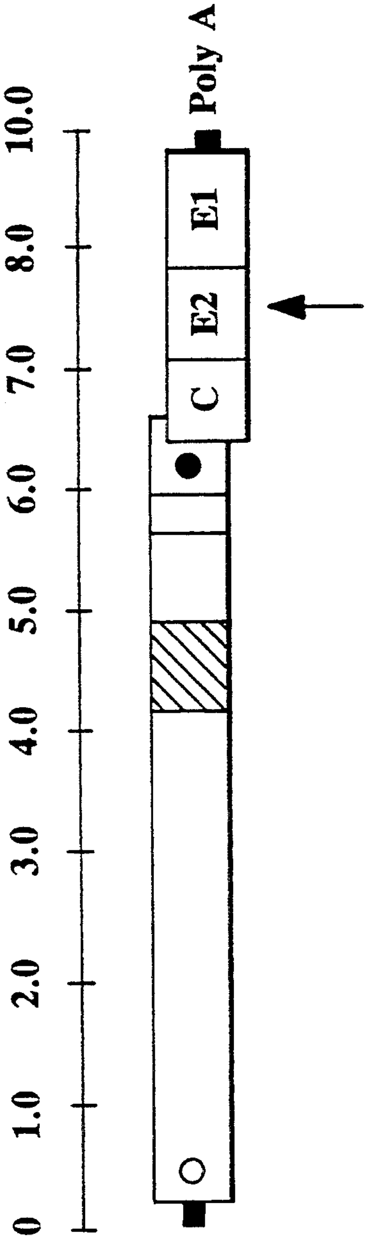
FIG. 1 is a schematic representation of the rubella virus genome with arrows showing a region in which the sequence can be modified to decrease virulence without loss of infectivity and immunogenicity.

The entire rubella virus RNA genome has been sequenced, including the 5248 nucleotides at the 5′ terminus encoding non-structural proteins which are critical to infection by the virus, and an infectious cDNA clone has been constructed. Mutations made in one or more regions of the cDNA clone render the resultant RNA virus non-pathogenic. The non-pathogenic RNA virus is combined with a pharmaceutically acceptable carrier to form a vaccine.

As shown below in SEQ ID NO:1, the wild-type rubella virus genomic RNA is 9757 nucleotides in length, excluding the poly(A) tail, and has a high guanosine plus cytosine ratio (G+C) content (69.5%). The rubella virus genomic RNA contains two long open reading frames, a 5′ proximal open reading frame of 6656 nucleotides which most likely encodes the non-structural proteins and a 3′ proximal open reading frame of 3189 nucleotides which encodes the structural proteins. Within the 5′ proximal open reading frame are two amino acid motifs commonly associated with replicase and helicase function, indicating the importance of this open reading frame in viral RNA replication. A stretch of 46 nucleotides is located 224 nucleotides from the 5′ end of the genome. This sequence is similar to a sequence conserved among alphaviruses which is believed to play a role in RNA replication. The rubella genome also contains a 20 nucleotide stretch 20 nucleotides upstream from the subgenomic RNA start site which shares homology with a conserved alphavirus sequence. This sequence is believed to be the subgenomic RNA promoter.

The predicted amino acid sequence of the rubella virus genome is shown below in SEQ ID NO:2 and SEQ ID NO:3. The 5′-proximal open reading frame begins at nucleotide 41 and terminates at position 6656 with an opal codon (UGA) followed 12 nucleotides downstream by a second inframe opal codon. The 5'-proximal open reading frame is 6615 nucleotides in length and encodes a 2205-amino acid polypeptide. The 3'-proximal open reading frame begins at nucleotide 6507 and ends at nucleotide 9696. It is 3189 nucleotide in length and encodes a polypeptide of 1063 amino acids which is cleaved into at least three structural proteins, C, E1 and E2, as discussed above.

As shown in FIG. 1, the two open reading frames overlap by 149 nucleotides and are in different translational frames. The schematic depression of the structural protein open reading frame relative to the nonstructural protein open reading frame of the rubella genome reflects this overlap. The open circle indicates the RNA start site for the entire rubella genome whereas the closed circle indicates the subgenomic RNA start site. The hatched box indicates the region of the helicase amino acid motif, and the shaded box indicates the replicase motif. The letters C, E2 and E1 represent the genes for the structural capsid, envelope 2 and envelope 1 glycoproteins respectively. The small black region at the 5' end of the genome represents a 5' cap while the small black region at the 3' end represents the poly(A) tail.

The present invention will be further described with reference to the following description of the isolation and characterization of the RNA sequence and the infectious cDNA clone for the rubella virus RNA genome. The teachings of the references describing in detail the methods used in the isolation, characterization, and modification of the RNA sequences are specifically incorporated herein by reference.

RNA isolation:

Virion RNA from the Therien strain of rubella virus was isolated by phenol-chloroform extraction of virions purified as described by Waxham, M. N. and Wolinsky, J. S., *Virology* 126:194–203 (1983). Intracellular RNA was extracted from infected Vero cells (m.o.i.=0.1) at 72 hr postinfection as described by Frey, T. K., *Virology,* 154:228–232 (1986). The extracted RNA was chromatographed over oligo(dT) cellulose. After ethanol precipitation, the poly(A)+ fraction was dissolved in 90% DMSO and heated at 55° C. for 5 min to denature double-stranded RNA replicative forms and intermediates which bind to oligo(dT) cellulose. The DMSO-denatured RNA was ethanol precipitated twice and dissolved in 0.01M Tris (pH 8.0), 0.001M EDTA.

Derivation and sequencing of cDNA clones:

Virion RNA was used as the template for first-strand cDNA synthesis primed with random deoxyhexamers (Pharmacia Fine Chemicals, Piscataway, N.J.) as described by Rice, C. M., et al., *Science* 229:726–733 (1985). Second-strand DNA synthesis, deoxycytidine (dC) tailing of the double-stranded cDNA with terminal transferase, annealing of dC-tailed cDNA with dG-tailed pUC 9, and transformations were done as described by Frey, et al., *Virology* 154:228–232 (1986) with the following modifications: double-stranded cDNA was chromatographed on a Sepharose™ CL-4B column (Pharmacia) to eliminate cDNAs less than 700 nucleotides in length, as described by Eschenfeldt, W. H. and Berger, S. L., Purification of large double-stranded cDNA fragments In "Methods in Enzymology" S. L. Berger and A. R. Kimmel, Eds., Vol 152:335–337 Academic Press, New York (1987), the teachings of which are incorporated herein, and transformed using competent DH5-α cells (Bethesda Research Labs, Bethesda, Md.).

Colonies with cDNAclones containing sequences overlapping the 3'-terminal 4508 nucleotides of the genome, described by Frey, T. K. and Marr, L. D., *Gene* 62:85–99 (1988), were identified by colony blot hybridization using as probes $^{32}$p-labeled restriction fragments and oligonucleotides from the 5' end of this sequence. This set of cDNA clones was restriction mapped and a restriction fragment from the 5' end of this set of clones was used as a probe to isolate new overlapping clones. Eighteen clones were identified and mapped which covered the region between 4500 nucleotides from the 3' end of the genome and the 5' end of the genome.

Sequencing strategy:

The cDNA inserts from eight clones representative of the region to be sequenced were subcloned into M13 for sequencing. Subcloning by use of convenient restriction sites, shotgun cloning of sonicated DNA, described by Bankier, A. T. and Barrell, B. G., *Nucleic Acid Biochem.* B508:1–34 (1983), and exonuclease III digestion to produce directional deletions, as described by Henikoff, S., *Gene* 28:351–359 (1984), the teachings of which are incorporated herein, were all employed. Several gaps which remained were sequenced using synthetic oligonucleotide primers on the appropriate templates. Oligonucleotides were synthesized using an Applied Biosystems Model 381A DNA Synthesizer. All sequencing was done by dideoxy sequencing, as described by Sanger, F., et al., *Proc. Natl. Acad. Sci. USA* 74:5463–5467 (1977), using the procedure recommended by Sequenase Version 2.0 kit (United States Biochemical Corp., Cleveland, Ohio) with [$^{32}$S]dATP label and 7-deaza-dGTP in place of dGTP.

Primer extension and dideoxy sequencing from an RNA template were both performed on poly(A)+-RNA from rubella-infected cells using as a primer a 5'-$^{32}$P-labeled oligonucleotide with the sequence dTGGTCTCTTACCCAACT (SEQ ID NO:4), which is complementary to nucleotides 101 to 117 of the genomic RNA. The primer extension reaction was done as described by Frey, T. K., et al., *Virology* 168:191–194 (1989), while RNA sequencing was done by dideoxy sequencing modified for an RNA template using the method of Rico-Hesse, R., et al., *Virology* 160:311–322 (1987), and Zimmern, D. and Kaesberg, P., *Proc. Natl. Acad. Sci. USA* 75:4257–4261 (1978).

Computer analysis:

The analysis of the sequence was performed on the Centers for Disease Control VAX using the University of Wisconsin GCP package, designed by Devereux, J., et al., *Nucl. Acids. Res.* 12:387–395 (1984).

Isolation of infectious cDNA clone:

A cDNA copy of the complete rubella genome RNA was assembled in a plasmid with an SP6 RNA polymerase promoter immediately adjacent to the 5' end of the cDNA. RNA transcripts from the contruct were produced. As a stringent assay to ascertain that the transcripts which appeared to be full length by agarose gel electrophoresis were indeed full length, Northern blot analysis was done on the transcripts using as a probe a radiolabeled oligonucleotide complementary to the 3' terminal 30 nucleotides of the rubella genome. Transcripts from the construct hybridized with the 3' terminal probe.

The following strategy was used to isolate an infectious clone, based on the nucleotide sequence. However, it would have been very difficult to make the clone from the sequence, without the cDNAs to combine to make the clone, and the addition of two nucleotides at the 5′ end.

Figure 2A:
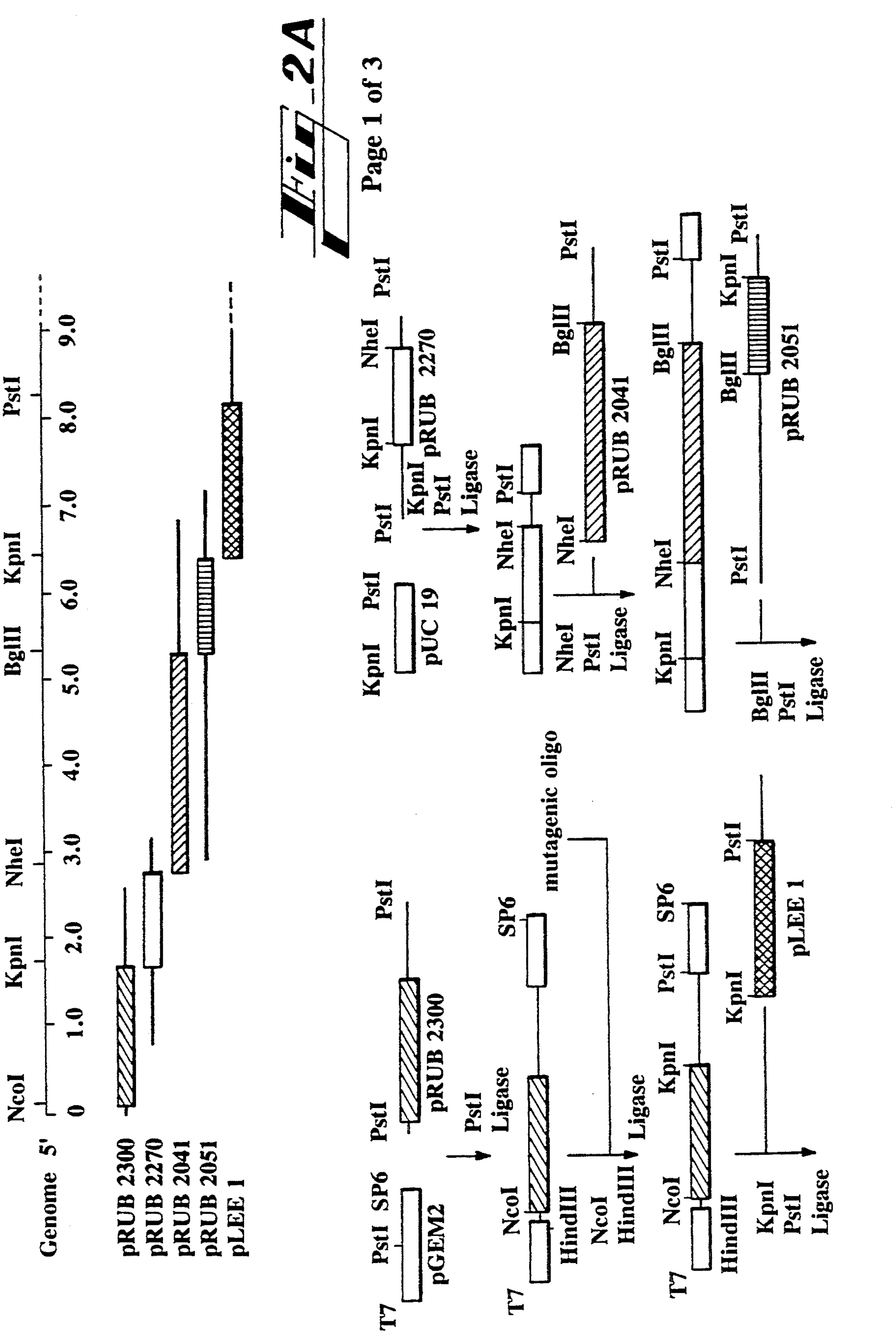
FIG. 2*a* is a schematic of the construction strategy of a non-infectious total genomic construct of the rubella virus, Robo 1, showing the mutagenic oligonucleotide (SEQ ID NOS: 5–6) and Primers 1–6 (SEQ ID NOS: 7–12)
Figure 2A:
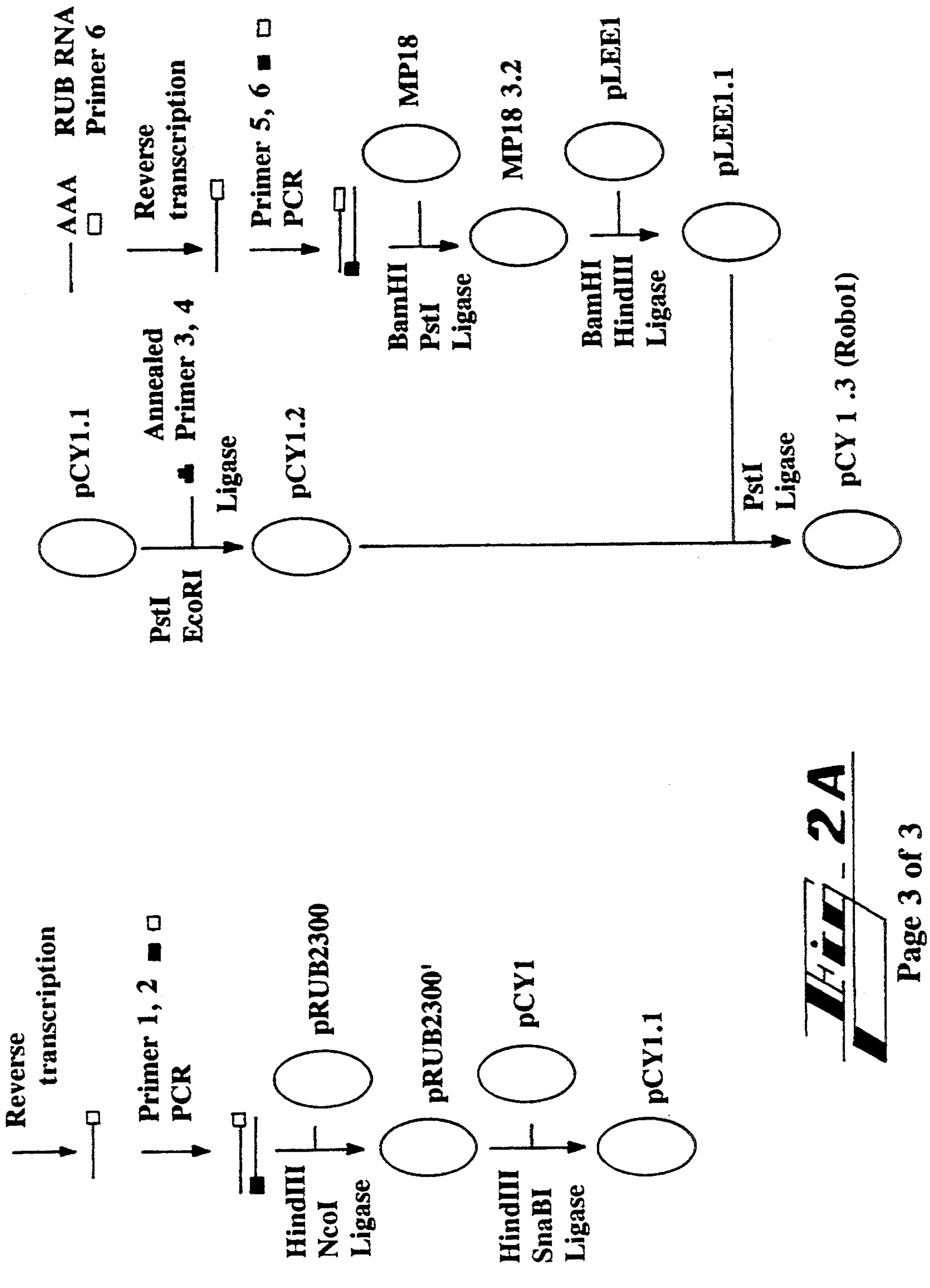
Figure 2B:
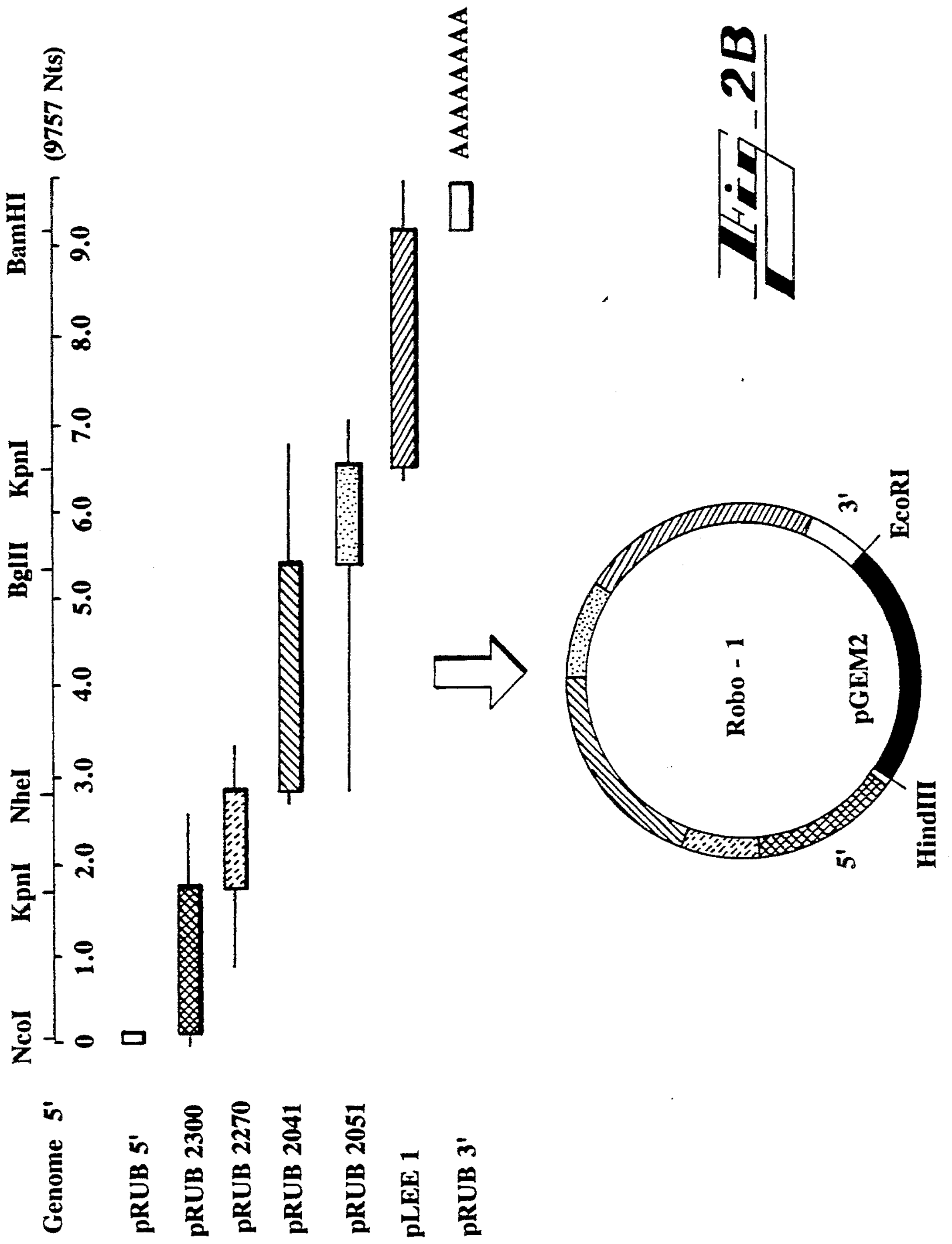
FIG. 2*b* is a schematic of the relative locations of each cDNA derived from the clones and the oligonucleotides used to modify the 3′ and 5′ ends.

The strategy and resulting construct are shown in FIGS. 2*a* and 2*b*. Four overlapping cDNAs derived as described above for sequencing of the 5248 5′ terminal nucleotides, a construct pLEE 1 which contained the structural protein coding regions derived as described by Frey, et al., (1986) and Frey and Marr (1988), the teachings of which are specifically incorporated herein, 40 nucleotides at the 5′ end synthesized with a DNA synthesizer (Applied Biosystems) and approximately 50 nucleotides at the 3′ end synthesized with a DNA synthesizer, were combined to form a construct Robol. Transcripts of this construct were not infectious.

Figure 3:
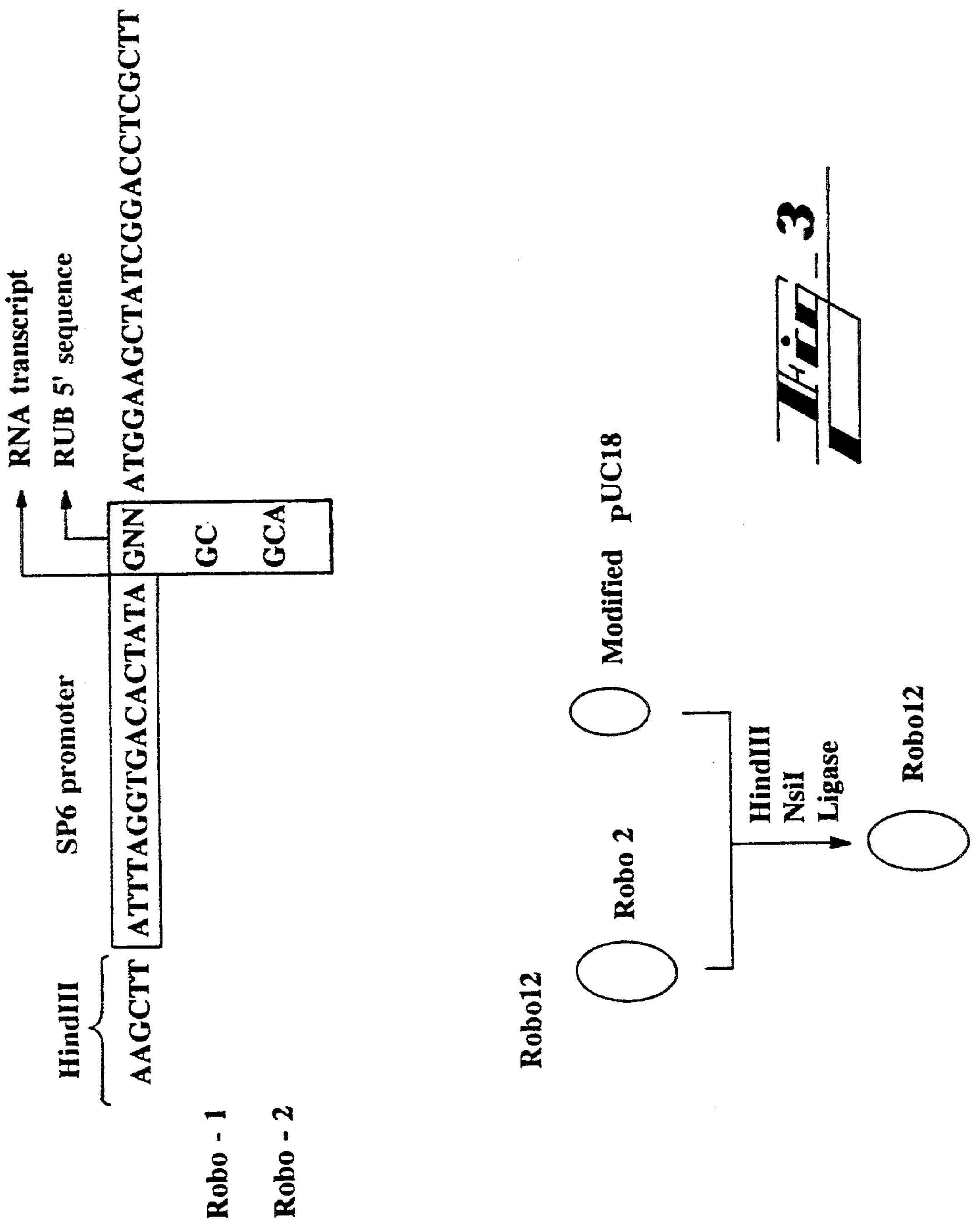
FIG. 3 is a schematic of modifications to the construct Robo1 of FIG. 2 to produce an infectious clone, Robo12 showing a portion of the 5′ end of the sequence (SEQ ID NO:13).

As shown in FIG. 3, two subsequent modifications, adding two nucleotides, C and A, at the 5′ end and removing one SP6 promoter at the 3′ end of the construct (leaving the SP6 promoter immediately adjacent the 5′ end) by cleaving with restriction enzymes to remove the construct in pGEM2, which contains an SP6 promoter, and inserting the construct into pUClS, yielded Robo12, transcripts of which were infectious. It appears that the addition of the CA at the 5′ end was crucial to making an infectious clone. This portion of the sequence had not previously been reported.

BHK-21 cells obtained from Dr. Charles M. Rice, Department of Microbiology and Immunology, Washington University School of Medicine, St. Louis, Mo., were transfected with the transcripts using lipofectin-mediated transfection techniques described by Rice, C. M., Graloue, A., Galler, R., Chambers, T. J., Transcription of infectious yellow fever RNA from full-length cDNA templates produced by in vitro ligation. *The New Biologist* 1, 285–296 (1989). (BHK-21 cells are available from the American Type Culture Collection. Lipofectin can be purchased from Bethesda Research Laboratories Inc., Gaithersburg, Md.) To detect the production of rubella virus in transfected BHK-21 cells, culture fluid was harvested and used to infect Vero cells obtained from the American Type Culture Collection. Vero cells were cultured at 35° C. under 4% $CO_2$ in Eagle Minimal Essential Medium containing Earle's salts and supplemented with 10% tryptose phosphate and 5% fetal bovine serum. Streptomycin was also added to minimize bacterial contamination.

Rubella virus was recovered from Vero cells infected with culture fluid from BHK-21 cells transfected with RNA extracted from virions and with RNA transcribed from the SP6 genomic construct, demonstrating that the cDNA clones were infectious.

Mutagenesis of cDNA clone:

The infectious cDNA clone can be modified in one or more of several ways to render it less virulent, while retaining infectivity and immunogenicity. Most preferably, a mutation or mutations are made to render the virus non-persistent. A non-persistent virus is defined herein as one that becomes non-virulent after the initial infection and development of an immune response but before the onset of arthritis or neurological impairment. As an example, non-persistance can be measured by the absence of viral penetration of synovial fluid.

In the preferred embodiment, a mutation is made in the E2 gene as shown in FIG. 1. Rubella virus is unique among enveloped viruses in that it buds both at intracellular membranes and at the cytoplasmic membrane, as reported by Bardeletti, G., et al., *Intervirology* 11:97–103 (1979). Rubella virus nucleocapsids form in association with membranes at the site of budding. Evidence suggests that the intracellular budding occurs at the endoplasmic reticulum and the Golgi apparatus. During intracellular budding, the rubella virus glycoproteins are retained at both sites for aprolonged period of time, six hours or greater, leading to delayed appearance of viral glycoproteins at the cell surface. It is believed that the E2 protein mediates the interaction of the C protein with these intracellular membranes to form intracytoplasmic vacuoles. These vacuoles may allow the rubella virus to persist in the presence of a humoral immune response. Therefore, mutations in the E2 gene or deletion of the entire gene for E2 should adversely affect persistence.

A mutation or mutations may also be made to render the virus incapable of binding to or crossing the placenta to infect a fetus. Placental binding or crossing can be measured by labelling the mutated virus with detectable substances such as radioactive or fluorescent labels and measuring the incorporation of those substances onto or across placental tissue.

The mutations are created using standard recombinant molecular biology techniques known to those skilled in the art such as linker-insertion mutagenesis, site-directed mutagenesis or homologous recombination. These techniques are described by, for example, Maniatis, T., Fritsch, E. F. and Sambrook, J., "Molecular cloning: A laboratory manual", (Cold Spring Harbor Laboratory, Cold Spring Harbor, N.Y. 1989).

Production and Screening of modified virus for decreased virulence:

The modified cDNA clone is placed within a vector, preferably a bacterial plasmid such as pUC 19, pGEM, or PBR-322 (all available from Promega Biotec, Madison, Wis.) adjacent to a bacteriophage RNA polymerase promoter sequence such as the SP6 RNA polymerase (Promega Biotec) such that RNA copies of the rubella virus DNA can be synthesized in vitro. The vector is chemically introduced into susceptible culture cells, for example, *E. coli*, for amplification and production of large amounts of the cDNA clone. For use, the purified infectious clone is restricted with a restriction endonuclease such as Nsi 1 (New England Biolabs, Beverly, Mass.) for linearization at the termination of the rubella virus cDNA sequences. The linearized plasmid is then transcribed with an RNA polymerase such as SP6 RNA polymerase, which results in production of RNA transcripts templated from the rubella virus cDNA sequence in the non-pathogenic infectious clone.

When an appropriate amount of the infectious clone RNA transcript is transfected into susceptible cells by transfection procedures known to those skilled in the art, less virulent rubella virus is recovered from the culture fluid within several days incubation. Preferably, an amount ranging from 0.5 to 1.5 micrograms of the infectious clone transcript is transfected into BHK-21 cells by lipofectin-mediated transfection. The identity of the virus recovered from the transfected cells can be confirmed by sequencing a specific region of the infectious clone in which a mutation exists which distinguishes it from the wild-type virus.

The less virulent rubella virus is then combined with a pharmaceutically acceptable carrier to provide a safe, effective rubella virus vaccine. The carrier can be oil, water, saline, phosphate buffer, polyethylene glycol, glycerine, propylene glycol, and combinations thereof, or other vehicles routinely used by the pharmaceutical industry for these purposes. The vaccine is usually provided in lyophilized form and therefore is free of preservatives.

It will be understood by those skilled in the art that modified cDNA for other DNA or RNA viruses could be inserted into the vector in combination with the rubella virus cDNA to make a vaccine effective in immunizing a patient against more than one virus. For example, the modified cDNA of RNA viruses such as hepatitis C or Dengue fever virus could be inserted into the vector to produce a combined recombinant vaccine. Methods of administration:

The vaccine can be administered by any appropriate route, for example, orally, parenterally, intravenously, intradermally, intramuscularly, subcutaneously, or topically, in liquid or solid form, which results in infection and elicitation of an immune response against the wild-type rubella virus. The vaccine is preferably administered subcutaneously at a concentration range from $10^2$ to $10^4$ $TCID_{50}$/person. (TCID is an abbreviation for tissue culture infectious doses.) Preferably the vaccine is provided to the physician in a lyophilized form, is reconstituted in an appropriate solvent such as deionized water or saline and administered as a single injection.

Modifications and variations of the infectious modified rubella virus, method of making a less virulent rubella vaccine and methods for use thereof will be obvious to those skilled in the art from the foregoing detailed description of the invention. Such modifications and variations are intended to come within the scope of the appended claims.

We claim:

1. An isolated DNA molecule comprising a nucleotide sequence encoding an infectious rubella virus.

2. The molecule of claim 1 wherein the DNA sequence corresponds to the RNA sequence of SEQ ID NO:1.

3. The molecule of claim 1 further comprising a vector, wherein the vector enables replication of the nucleotide sequence.

4. The molecule of claim 3 wherein the vector is a bacterial plasmid.

5. A method of producing a rubella virus comprising the steps of:

a. inserting a DNA molecule having a nucleic acid sequence encoding an infectious rubella virus into a plasmid;

b. transcribing the DNA into linear RNA;

c. transfecting cells with the nucleic acid transcript; and d. recovering rubella virus from the transfected cells.

* * * * *